United States Patent [19]

Shah et al.

[11] Patent Number: 5,310,559

[45] Date of Patent: * May 10, 1994

[54] DEVICE FOR CONTROLLED RELEASE AND DELIVERY TO MAMMALIAN TISSUE OF PHARMACOLOGICALLY ACTIVE AGENTS INCORPORATING A RATE CONTROLLING MEMBER WHICH COMPRISES AN ALKYLENE-ALKYL ACRYLATE COPOLYMER

[75] Inventors: Kishore Shah, Bridgewater; Agis Kydonieus, Kendall Park, both of N.J.

[73] Assignee: Hercon Laboratories Corporation, New York, N.Y.

[*] Notice: The portion of the term of this patent subsequent to Jul. 19, 2005 has been disclaimed.

[21] Appl. No.: 964,478

[22] Filed: Oct. 21, 1992

Related U.S. Application Data

[63] Continuation of Ser. No. 434,629, Nov. 13, 1989, abandoned, which is a continuation of Ser. No. 292,040, Dec. 30, 1988, abandoned, which is a continuation of Ser. No. 123,051, Nov. 19, 1987, abandoned, which is a continuation-in-part of Ser. No. 847,635, Apr. 3, 1986, Pat. No. 4,758,434, which is a continuation-in-part of Ser. No. 657,911, Sep. 5, 1984, abandoned, which is a continuation-in-part of Ser. No. 413,658, Sep. 1, 1982, abandoned.

[51] Int. Cl.$^5$ .............................................. A61F 13/00
[52] U.S. Cl. ................................... 424/448; 424/449; 424/422; 424/424; 424/425
[58] Field of Search ............ 424/449, 422, 424, 425.1, 424/448; 526/329

[56] References Cited

U.S. PATENT DOCUMENTS

| | | | |
|---|---|---|---|
| 3,921,636 | 11/1975 | Zaffaroni | 128/260 |
| 3,965,255 | 6/1976 | Bloch et al. | 424/19 |
| 3,996,934 | 12/1976 | Zaffaroni | 128/268 |
| 4,060,084 | 11/1977 | Chandraeskeran | 424/449 |
| 4,150,109 | 4/1979 | Dick et al. | 424/28 |

(List continued on next page.)

FOREIGN PATENT DOCUMENTS 314738 3/1974 Austria .
930668 7/1973 Canada .

(List continued on next page.)

OTHER PUBLICATIONS

H. Mark et al.: "Encyclopedia of Polymer Science and Technology; Plastics, Resins, Rubbers, Fibers", vol. 10, 1969, J. Wiley, New York, US; p. 269.

(List continued on next page.)

*Primary Examiner*—Thurman K. Page
*Assistant Examiner*—Neil Levy
*Attorney, Agent, or Firm*—Sughrue, Mion, Zinn, Macpeak & Seas

[57] ABSTRACT

Described is a device for the controlled release and delivery to mammalian tissue of a pharmacologically active agent comprising:

(i) an impermeable backing member;

(ii) a control membrane lamina consisting essentially of a first polymeric composition of matter which consists essentially of at least one $C_2$–$C_4$ lower olefin-$C_1$–$C_8$ alkyl acrylate and/or methacrylate copolymer having 2–90% by weight of alkyl acrylate and/or methacrylate monomeric units, taken alone, or taken further together with in intimate admixture, a second polymeric composition consisting essentially of a $C_2$–$C_4$ polyalkylene corresponding to the $C_2$–$C_4$ lower alkylene of said copolymer, said second polymeric composition being compatible with said first polymeric composition of matter; and (iii) a pharmacologically active agent reservoir maintained there between comprising said pharmacologically active agent and a carrier therefor and, optionally, one or more excipients and/or enhancers; and (iv) means for maintaining said device in pharmacologically active agent transmitting relationship to the mammalian tissue to be treated.

31 Claims, 11 Drawing Sheets

U.S. PATENT DOCUMENTS

| | | | |
|---|---|---|---|
| 4,201,211 | 5/1980 | Chandraskeran | 424/449 |
| 4,356,288 | 10/1982 | Lewis et al. | 526/329 |
| 4,599,392 | 7/1986 | McKinny et al. | 424/449 |
| 4,615,699 | 10/1986 | Cole et al. | 424/449 |
| 4,758,434 | 7/1988 | Kydonieus et al. | 524/98 X |

FOREIGN PATENT DOCUMENTS

| | | |
|---|---|---|
| 0139127 | 5/1985 | European Pat. Off. |
| 0186077 | 7/1986 | European Pat. Off. |
| 2314509 | 9/1973 | Fed. Rep. of Germany |
| 2362123 | 6/1974 | Fed. Rep. of Germany |
| 2309202 | 8/1974 | Fed. Rep. of Germany |
| 620122 | 11/1980 | Switzerland |
| 2155335 | 9/1985 | United Kingdom |

OTHER PUBLICATIONS

Japanese Patents Gazette, Section Ch: Chemical, Week ED37, 1982, ref. No. 775533, Derwent Publications, London, GB; for JP-A-57-126416 (Sekisui Chemi Ind K.K.) Aug. 6, 1982.

Chemical Abstracts, vol. 101, Nov. 1984, Columbus, Ohio, USA for J. Szlaski and Z. Zakrzewski, "Sustained-action propranolol tablets", p. 387, col. 2, abstract No. 177448g & Acta Pol. Pharm. 1983 40(5–6), 615–620.

Patent Abstracts of Japan, unexamined applications, C section, vol. 10, No. 49, Feb. 26, 1986, p. 31 C 330, for Kokai-No. 60-193 918 (Mitsui Toatsu Kagaku K.K.).

Shah et al "Hercon Technology for Transdermal Delivery of Drugs" Journal of Biomaterials Applications, vol. 1–Oct. 1989 pp. 239–273, Technomic Pub. Co., Inc.

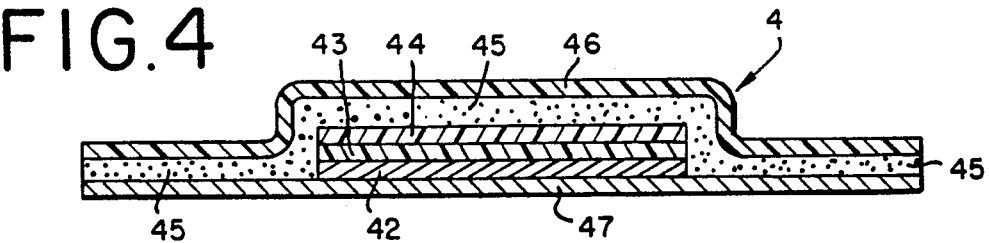
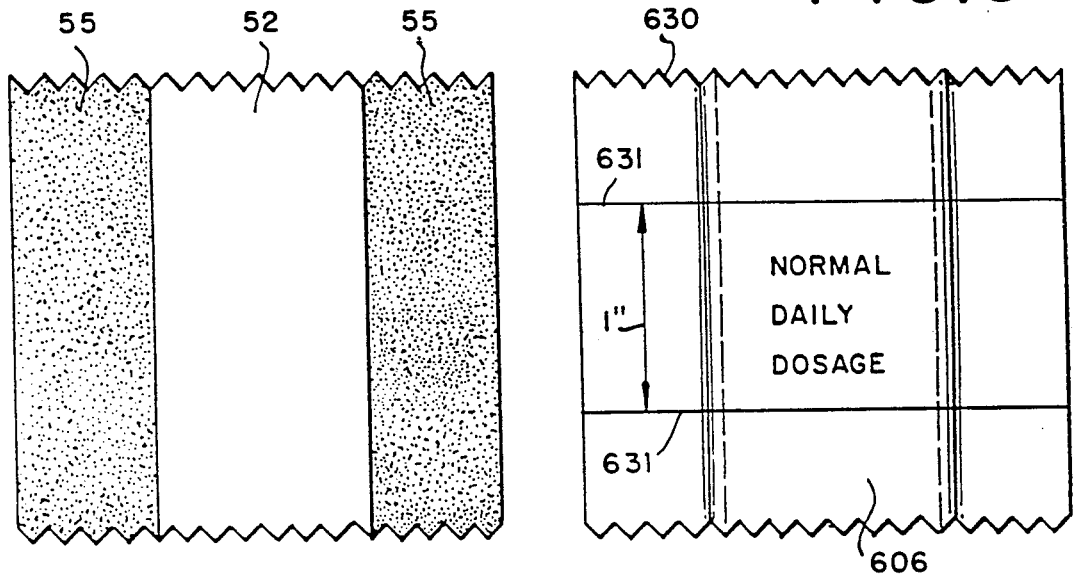
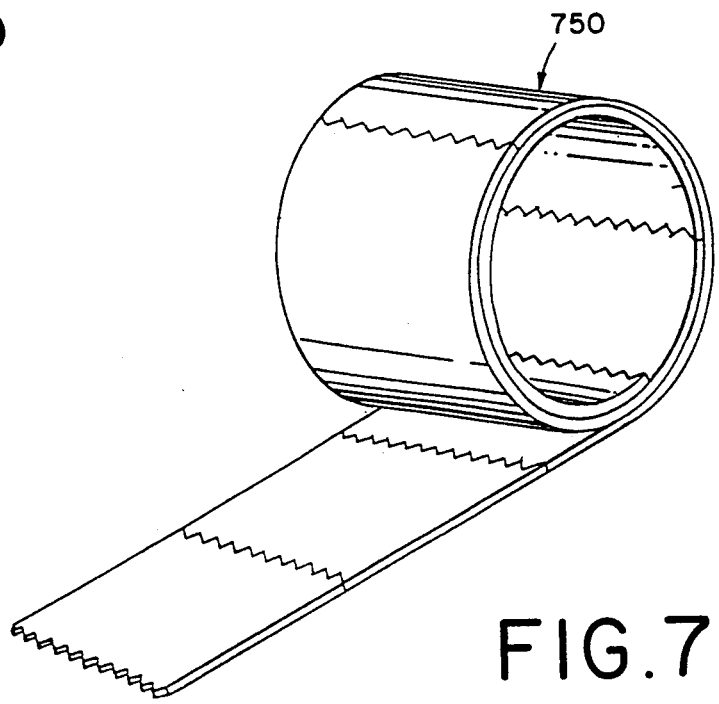

IR SPECTRUM

DEVICE FOR CONTROLLED RELEASE AND DELIVERY TO MAMMALIAN TISSUE OF PHARMACOLOGICALLY ACTIVE AGENTS INCORPORATING A RATE CONTROLLING MEMBER WHICH COMPRISES AN ALKYLENE-ALKYL ACRYLATE COPOLYMER

This is a continuation of application Ser. No. 07/434,629 filed Nov. 13, 1989 now abandoned, which is a continuation of application Ser. No. 07/292,040 filed Dec. 30, 1988 abandoned, which is a continuation of application Ser. No. 07/123,051 filed Nov. 19, 1987 abandoned, which is a continuation-in-part of application Ser. No. 06/847,635 filed Apr. 3, 1986 now U.S. Pat. No. 4,758,434, which is a continuation-in-part of application Ser. No. 06/657,911 filed Sep. 5, 1984 abandoned, which is a continuation-in-part of application Ser. No. 06/413,658 filed Sep. 1, 1982 abandoned.

BACKGROUND OF THE INVENTION

1. Field of the Invention

This invention relates broadly to articles of manufacture for administration of pharmacologically active substances, transdermally and by means of implant (e.g., subdermal implant).

The system comprises a backing member substantially impermeable to the pharmacologically active agent, a pharmacologically active agent reservoir member consisting essentially of a pharmacologically active agent and a carrier therefor and a rate controlling member which is a lamina consisting essentially of a first polymeric composition of matter which consists essentially of at least one $C_2$-$C_4$ lower olefin-$C_1$-$C_8$ alkyl acrylate and/or methacrylate copolymer having 2-90% by weight of alkyl acrylate and/or methacrylate monomeric units, taken alone, or further taken together with, in intimate admixture, a second polymeric composition consisting essentially of a $C_2$-$C_4$ polyalkylene corresponding to the $C_2$-$C_4$ lower alkylene of said copolymer, said second polymeric composition being compatible with said first polymeric composition of matter.

2. The Prior Art

Many prior art articles of manufacture have been disclosed for controlled release delivery of various drugs including transdermal delivery of nitroglycerin and timolol as well as clonidine. Indeed, prior art devices exist for high flux transdermal delivery of drugs over an extended period of time comprising in combination:

(a) an impermeable backing member;
(b) a pharmacologically active agent rate controlling membrane;
(c) a pharmacologically active agent reservoir maintained there between with the reservoir composition comprising a carrier and the pharmacologically active agent; and
(d) means for maintaining the system in pharmacologically active agent transmitting relationship to the skin.

Pharmacologically active agent release rate controlling membranes composed of compositions of matter consisting essentially of olefin-alkyl acrylate copolymers taken alone or further together in intimate admixture with olefin polymers have not been disclosed and are unknown in the prior art.

European Patent 186,071 assigned to Merck and Co., Inc. published on Jul. 2, 1986 discloses a system for administering timolol for an extended period comprising a backing member substantially impermeable to timolol, a timolol reservoir member consisting essentially of timolol as the drug and a carrier therefor and a rate controlling member which can be microporous polypropylene, ethylene-vinyl acetate copolymer, a silicone polymer or a polyurethane polymer. The European Patent 186,071 indicates that by the system disclosed transdermal application of timolol may be accomplished with substantially no irritation to the skin.

U.S. Pat. No. 4,060,084 assigned to Alza Corporation discloses a method and therapeutic system in the form of a bandage for providing chemotherapy transdermally by administering certain drugs to unbroken skin in an initial priming dose that quickly brings the systemic concentration of drug to a therapeutic level, followed by a substantially constant dosage that holds the level, U.S. Pat. No. 4,060,084 discloses a bandage which is a four-layer laminate of, from the top: a protective backing; a drug reservoir lamina that is a source of constant dosage; a microporous membrane that controls the constant dosage rate; and an adhesive layer that is the source of the priming dose and the means by which the bandage is attached to the skin. However, disclosed for use in fabricating the membrane are polymers such as polypropylene, polyethylene, polyvinyl chloride, cellulose acetate, cellulose nitrate, polycarbonates and polyacrylonitrile. No mention is made of polyacrylates or acrylate-polyolefin copolymers for use as the controlling membrane in U.S. Pat. No. 4,060,084.

U.S. Pat. No. 4,615,699 issued on Oct. 7, 1986 assigned to Alza Corporation discloses a high flux transdermal nitroglycerin therapeutic system capable of delivering nitroglycerin through intact human skin at rates of 40 micrograms/$cm^2$hr. and preferably in the range of 50-150 micrograms/$cm^2$hr. It is indicated that ethanol delivered at a rate of from 250-500 micrograms/$cm^2$hr. is employed as a permeation enhancer for the nitroglycerin and a rate controlling membrane formed from ethylene vinyl acetate having a vinyl acetate content greater than 11% and preferably between 12-18% "provides the appropriate rate control for both the drug and the permeation enhancer", U.S. Pat. No. 4,615,699 does not infer the utilization of the copolymers or copolymer-polymer mixtures which form the basis of the instant invention.

U.S. Pat. No. 4,201,211 issued on May 6, 1980 discloses a therapeutic system in the form of a skin patch that administers clonidine transdermally in an initial priming dose of 10 to 30 micrograms/$cm^2$ of skin that brings the concentration of clonidine in the blood to a level sufficient to elicit alpha-adrenergic stimulation without intolerable side effects followed by a substantially constant continuous dosage in the range of 0.1 to 100 micrograms/hr. that maintains the level. The system is a four-layer laminate of, from the top: a protective backing; a gelled mineral oil-polyisobutene-clonidine reservoir lamina that is the source of the clonidine for the continuous constant dosage; a microporous membrane that controls the constant dosage rate; and a gelled, mineral oil-polyisobutene-clonidine contact adhesive layer that is the source of the clonidine for the priming dose and the means by which the system is attached to the skin, U.S. Pat. No. 4,201,211 does not disclose the use or infer the use of the acrylate-olefin copolymer for the control membrane; that is, the membrane that controls the dosage rate.

Indeed, nothing in the prior art discloses the utilization in control release pharmacologically active drug devices of a control membrane composed of an acrylate-olefin copolymer or mixtures thereof with polyolefins as described and claimed in the instant invention.

Shah, et al, Journal of Biomaterials Applications, Vol. 1, October, 1986, pages 239–273 discloses a multi-layered laminated polymeric structure for controlled drug delivery in which a layer of vinyl chloride copolymer or terpolymer containing the drug is sandwiched between two or more layers of polymeric films. Shah, et al discloses that the drug is released from the device at a controlled rate by a process of diffusion through the reservoir and one of the outer layers which can function as a rate controlling membrane. Shah, et al discloses at page 259, that:

"The rate controlling membranes investigated were olefinic copolymers containing a polar modifier,"

The Shah, et al paper was published subsequent to the filing date of parent application, Ser. No. 847,635 filed on Apr. 3, 1986, now U.S. Pat. No. 4,751,438.

Furthermore, Canadian Patent No. 930,668 discloses a bandage for administering drugs comprised of a backing member, a pressure sensitive adhesive, and at least one reservoir disposed between the backing member and pressure sensitive adhesive. The reservoir is comprised of a systemically active drug formulation confined within a wall member, the wall member being formed from a drug release controlling material. The reservoir can be in the form of discrete microcapsules or distinct reservoir compartments or layers. The reservoir can also be in the form of walled containers having one or more interior drug-containing chambers, as well as solid matrices having a systemically active drug distributed therethrough. The Canadian patent discloses a wide variety of materials which can be used to form the reservoir. Among the materials mentioned are silicone rubbers, hydrophilic polymers of monoesters of an olefinic acid, polyvinylalcohol, polyvinylacetate, plasticized polyvinylchloride, plasticized nylon, collagen, modified collagen, gelatin, and waxes such as polyethylene wax, oxidized polyethylene wax, hydrogenated castor oil and the like, with the silicone rubbers being preferred. The Canadian patent does not contain any examples showing the use of plasticized polyvinyl chloride.

Similarly, Zaffaroni, U.S. Pat. No. 3,921,636 issued on Nov. 25, 1975 discloses a drug delivery device for administering a drug at a controlled rate for a prolonged period of time comprising a plurality of reservoirs containing drug distributed through a matrix. The reservoirs and the matrix are formed of materials permeable to passage of the drug. The rate of drug permeation from the reservoir is lower than the rate of permeation through the matrix so that release from the reservoir is the drug release controlling step. Thus, Example 6, at column 15, lines 5–30 of U.S. Pat. No. 3,921,636 relates to a polyvinyl chloride resin containing plasticizer and prednisolone disodium phosphate thusly:

"A drug delivery device for the controlled, oral administration of water-soluble prednisolone is prepared as follows: first, a plurality of drug reservoirs comprising porous, discrete particles of polymerized poly(vinyl chloride) of about 100 microns diameter are prepared by mixing 100 g of suspension grade poly(vinyl chloride) resin with 50 g of octyl diphenyl phosphate and 10 g of prednisolone disodium phosphate at room temperature into a sticky, wet mass. Next, the temperature of the mixture is raised to 80° C. for about 3 to 7 minutes, while stirring, to form dry, free flowing, discrete drug reservoirs. The reservoirs are uniformly dispersed through a matrix by mixing 50 g of reservoirs containing the prednisolone with 140 g of polydimethylsiloxane, 10 g of silicone oil, and 0.5 g of stannuous octoate. After mixing the ingredients, the mixture is charged into pill molds and allowed to cure for 30 minutes. Oral administration of the resulting device yields a controlled essentially constant rate of release of prednisolone phosphate to the gastrointenstinal tract to give a more uniform blood level of prednisolone over a longer period of time than is achieved when prednisolone alcohol is administered by standard prior art pills."

U.S. Pat. No. 4,150,109 (Dick, et al) issued on Apr. 17, 1979 entitled "Device for Protecting Animals from Ectoparasites" discloses and claims:

"In an animal collar for controlling fleas and ticks on cats and dogs, a part of said animal collar being formed of a solid vinyl or vinylidene polymer matrix in which is dispersed a pesticidal composition, an improved pesticidal composition consisting essentially of:
(a) 0.5 to 15% by weight of an ethylenically unsaturated oil, and
(b) a mixture of diethyl O-(2-isopropyl-4-methyl-6-pyrimidinyl)thionosphosphate and diethyl O-(2-isopropyl-4-methyl-6-pyrimidinyl)phosphate,
wherein diethyl O-(2-isopropyl-4-methyl-6-pyrimidinyl) thionophosphate is 10 to 90% by weight of said mixture and diethyl O-(2-isopropyl-4-methyl-6-pyrimidinyl)phosphate is 90 to 10% by weight of said mixture."

wherein the "solid vinyl . . . matrix" and the plasticizers are described thusly:

"The macromolecular substance preferably has a weight of more than 1000; it is selected from the homopolymers and copolymers obtained starting from vinyl chloride, vinyl acetate, vinyl acetals, vinylalcohol, vinylbenzene and divinylbenzene and vinylidene chloride; the copolymers may, in addition, contain additional components such as ethylenic, propylenic, butadienic, isoprenic, acrylic and methacrylic components.

Preferably, the macromolecular substance is a polymer or copolymer of a vinyl compound such as, for example, the polyvinyl halides. The particularly preferred macromolecular substances are polymers or copolymers of vinyl chloride.

The macromolecular substance preferably contains one or more plasticizers.

The plasticizers are liquid esters with a vapour pressure of less than 0.0001 mm/Hg at 25° C. Some nonrestrictive examples of plasticizers are: diethyl, dimethyl, dipropyl, dibutyl, dihexyl, dioctyl and didecyl phthalate, dibutyl, diamyl, dinonyl, dioctyl, and didecyl adipate, dipropyl, dibutyl, dibenzyl and dioctyl sebacate, diethyl, dipropyl and dibutyl citrate, triphenyl and tricresyl phosphate and the triglycerides.

The preferred plasticizers are dibutyl phthalate and dioctyl adipate, which make it possible to obtain an arrangement with good flexibility, on the surface of which the active principle appears rapidly and regularly."

Furthermore, as is well known, polyvinyl chloride (PVC) is never used alone, but is always mixed with other ingredients before being processed. Polyvinyl chloride appeared initially to be an unpromising resin because of its thermal instability and high rigidity. PVC, however, was then discovered to form a rubber-like material when dissolved hot in high boiling solvents known as plasticizers and cooled to room temperature. PVC is now available in a number of different physical forms and types, and its manufacture depends on the form desired. Thus, PVC is available as a vinyl latex, a dispersion resin, or a general purpose resin. PVC latexes are true colloidal dispersions of submicrometer particles in water, stabilized by a surfactant system, and need plasticizers in order to form a continuous film. The PVC is vinyl latex is manufactured by emulsion polymerization.

Dispersion resins are produced by emulsion polymerization and are mixed with plasticizers to form a colloidal dispersion. Such dispersions are known as plastisols and are easily handled and readily pourable. When heated to a temperature of about 140° to 177° C., the plastisol is transformed to a homogeneous melt which, upon cooling to below 50° C., results in a tough flexible product. The PVC resins made by emulsion polymerization are hard spheres of particle size between about 0.05 and 20 microns, such as between 1 and 20 microns. They do not have the ability to absorb plasticizers. Therefore, a mixture containing, for example, 30% plasticizer and 70% PVC resin, produces a flowable liquid, known as "plastisol".

General purpose PVC resins are made by mass and suspension polymerization process, and comprise the largest amount of PVC resins produced, such as at least 80% of all PVC resins, and are used chiefly to make so-called 100% vinyl products by a variety of molding and extrusion techniques. Resins intended for flexible applications should have good uptake of plasticizer in a dry blending operation and contain more than 25% of a plasticizer system. PVC compounds that contain less than 25% plasticizers are referred to as semirigid compounds. The PVC resins manufactured by suspension and bulk polymerization are 50 to 200, such as 100 to 150 microns in diameter, and are like sponges. They are capable of absorbing large amounts of plasticizers, so that even a 50% plasticizer, 50% PVC resin composition would result in a non-flowing, solid material.

SUMMARY OF THE INVENTION

It is an object of the present invention to provide an article of manufacture which offers enhanced delivery capability of pharmacologically active agents over prior commercial devices (transdermal devices and subdermal implants used to administer subdermally pharmacologically active agents) by providing an article capable of efficaciously administering pharmacologically active agents directly from a reservoir in which the pharmacologically active agent is incorporated in relatively high concentrations, e.g., from 0.5% up to 35% and a relatively low rate over a relatively long period of time by means of the use of a specially designed control membrane which consists essentially of a first polymeric composition of matter which consists essentially of at least one $C_2$-$C_4$ lower olefin-$C_1$-$C_8$ alkyl acrylate and/or methacrylate copolymer have 2-90% by weight of alkyl acrylate and/or methacrylate monomeric units, taken alone or taken further together, in intimate admixture a second polymeric composition consisting essentially of a $C_2$-$C_4$ polyalkylene corresponding to the $C_2$-$C_4$ lower alkylene of said copolymer with the second polymeric composition being compatible with the first polymeric composition of matter.

This invention also enables the administration of a pharmacologically active agent such as clonidine or its salts, scopolamine or its salts; timolol, clenbuterol, nicotine and fentanyl to be achieved through an article of manufacture, e.g., an transdermal delivery device requiring contact with a relatively smaller area of a patient's tissue such as the epidermis in the case of a transdermal delivery device.

Thus, this invention is directed to an article of manufacture for the controlled release and delivery to mammalian tissue of a pharmacologically active agent comprising:

(i) an impermeable backing member;
(ii) a control membrane lamina consisting essentially of a first polymeric composition of matter which consists essentially of at least one $C_2$-$C_4$ lower olefin-$C_1$-$C_8$ alkyl acrylate and/or methacrylate copolymer having 2-90% by weight of alkyl acrylate and/or methacyrlate monomeric units taken alone or taken further together with, in intimate admixture a second polymeric composition consisting essentially of a $C_2$-$C_4$ polyalkylene corresponding to the $C_2$-$C_4$ lower alkylene of the first polymeric composition, the said second polymeric composition being compatible with the said first polymeric composition of matter;
(iii) a pharmacologically active agent reservoir maintained there between comprising said pharmacologically active agent and a carrier therefor (a) said pharmacologically active agent being physically and chemically compatible with said first polymeric composition of matter and (b) said first polymeric composition of matter being capable of permitting release of said pharmacologically active agent from said pharmacologically active agent reservoir at a rate lower than that previously obtained in prior art articles and from a reservoir containing a concentration of pharmacologically active agent higher than that previously used in prior art articles.

The controlled membrane lamina contains a polymeric composition of matter which contains the repeating monomeric units:

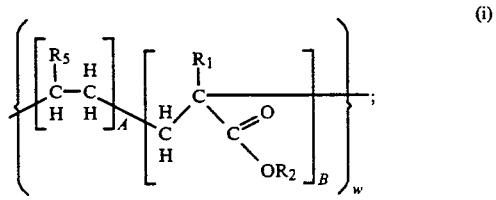

(i)

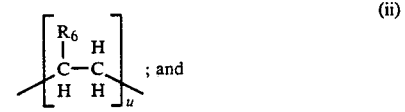

(ii)

-continued

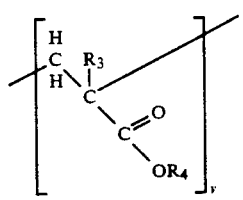

wherein R₅ and R₆ are the same or different hydrogen or methyl;

wherein R₁ and R₃ are the same or different hydrogen or methyl;

wherein R₂ and R₄ are the same or different methyl or ethyl;

wherein w, A, B, u and v are integers; and wherein the mole ratio of A+u:B+v varies about 10:90 to about 98:2.

Timolol has the structure:

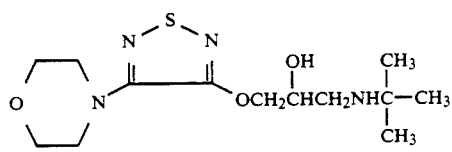

Clenbuterol has the structure:

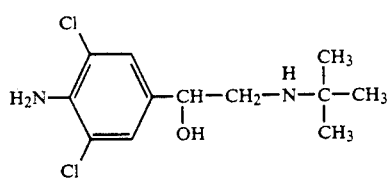

Clonidine has the structure:

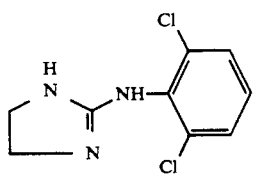

Scopolamine has the structure:

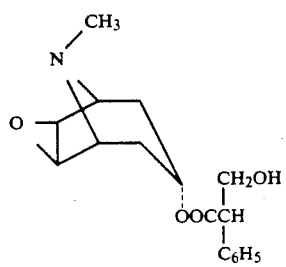

Nicotine has the structure:

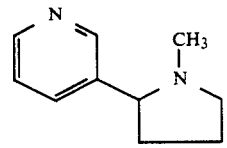

Fentanyl has the structure:

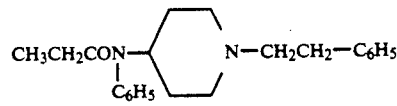

This invention also contemplates administration of such pharmacologically active agents orally.

BRIEF DESCRIPTION OF THE DRAWINGS

FIG. 4 is a cross-sectional view of a pharmacologically active agent delivery device in accordance with our invention.

FIG. 5 is a plan view of a strip of material in accordance with our invention viewed from the surface which is applied to the patient's skin.

FIG. 6 is a plan view of material in accordance with our invention viewed from the surface away from the surface which is applied to the patient's skin.

FIG. 7 is a perspective view of a roll of material in accordance with this invention.

DETAILED DESCRIPTION OF THE INVENTION

Figure 1:
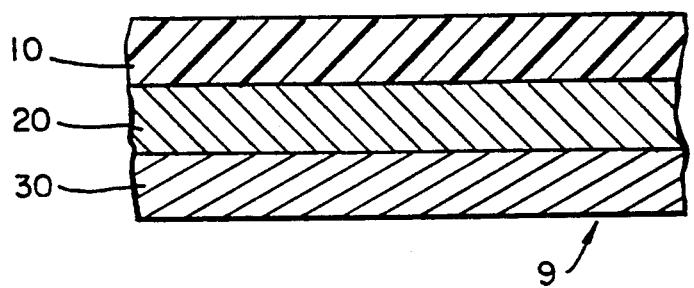
FIG. 1 is a cross-sectional view of a pharmacologically active agent delivery device in accordance with this invention having three layers; a backing layer, a reservoir layer and a rate controlling membrane (as used in Example I, infra).

The invention is described herein with respect to preferred embodiments including transdermal devices containing various pharmacologically active agents and subdermal devices including various pharmacologically active agents, which pharmacologically active agents include but are not limited to:

Timolol having the structure:

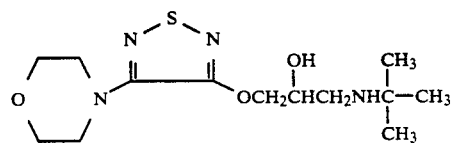

or its salts, such as its hydrogen maleate salt;
Clenbuterol having the structure:

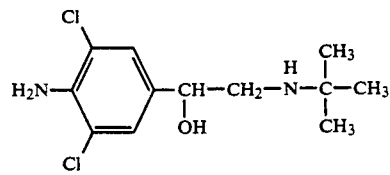

Clonidine having the structure:

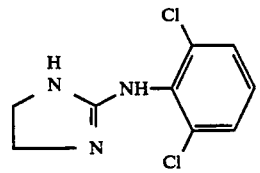

or its salts, such as its hydrochloride salt;
Scopolamine having the structure:

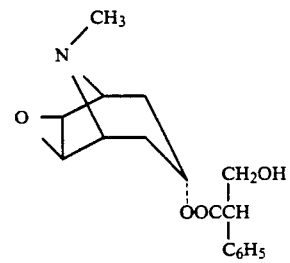

Nicotine having the structure:

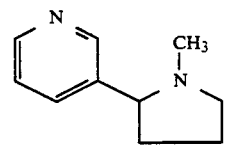

or its salts, such as its hydrochloride, dihydrochloride, iodides, sulfate, tartrate, acid tartrate, bitartrate, zinc chloride double salt monohydrate, and salicylate;
Fentanyl having the structure:

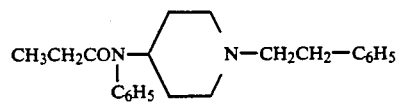

It will be understood that other embodiments may be employed within the spirit and scope of our invention.

The articles of our invention are useful for transdermal and subdermal administration of pharmacologically active substances and comprise reservoirs containing the pharmacologically active agent from which the pharmacologically active agent is delivered either subdermally or transdermally through mammalian tissue at a rate-controlled manner through a copolymeric rate-controlling membrane which consists essentially of at least one $C_2$–$C_4$ lower olefin/$C_1$–$C_8$ alkyl acrylate and/or methacrylate copolymer having 2–90% by weight of alkyl acrylate and/or methacrylate monomeric units taken alone or taken further together with in intimate admixture a third polymeric composition consisting essentially of a $C_2$-$C_4$ polyalkylene corresponding to the $C_2$-$C_4$ lower alkylene of the copolymer. Thus, the membrane used in conjunction with our invention consists of a polymeric composition of matter containing the repeating monomeric units:

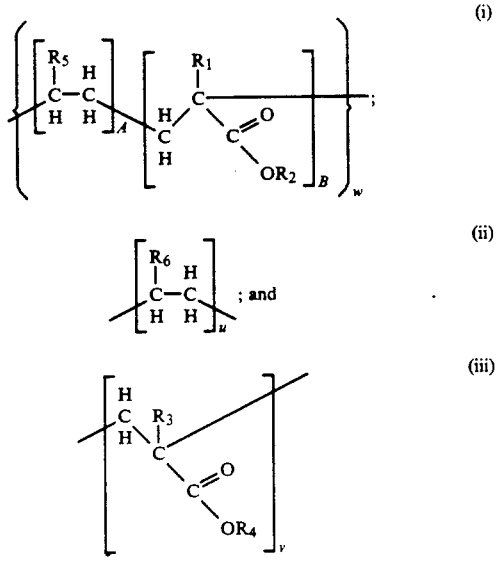

wherein $R_5$ and $R_6$ are the same or different hydrogen or methyl;

wherein $R_1$ and $R_3$ are the same or different hydrogen or methyl;

wherein $R_2$ and $R_4$ are the same or different methyl or ethyl;

wherein w, A, B, u and v are integers; and wherein the mole ratio of A+u: B+v varies about 10:90 to about 98:2.

The pharmacologically active agent-containing reservoir may be a polymeric reservoir, for example, a solid plasticized polyvinyl chloride (preferably in the form of a "vinyl plastisol") layer (consisting essentially of polyvinyl chloride and the plasticizer) for contacting a patient's skin or other membrane. The plasticized polyvinyl chloride layer may contain, for example, from about 20 up to about 60% by weight of a polyvinyl chloride resin which consists essentially of a vinyl chloride polymer containing, predominantly or completely, repeating vinyl chloride monomeric units and in an amount of less than about 10% other repeating vinyl units, e.g., repeating vinyl acetate units; from about 20% up to about 70% by weight of the composition of one or more plasticizers; from about 0.5 up to about 35% by weight of the total composition of a pharmacologically active substance and, optionally, other excipients, such as materials which will accelerate transdermal penetration as exemplified herein.

Such reservoir layers as useful in the instant invention are relatively weak and less than 1500 psi highly flexible and soft materials.

Referring to FIG. 1, the device 9 includes a backing 10; adhering to one surface of the backing a pharmacologically active agent-containing reservoir 20; and adhering to one side of the pharmacologically active-containing reservoir a rate controlling membrane 30.

Thus, for example, the pharmacologically active agent-containing reservoir may be composed of pharmacologically active agent, e.g., 2–10%; polyvinyl acetate (about 15%) and polyvinyl pyrrolidone (about 8%).

The rate controlling membrane may be composed of a copolymer of ethylene and methyl acrylate wherein the amount of ethylene monomeric units may vary from about 7% up to about 18%.

Referring to the device set forth in FIG. 1, this device is further shown to be utilized in Example I, infra.

Figure 2:
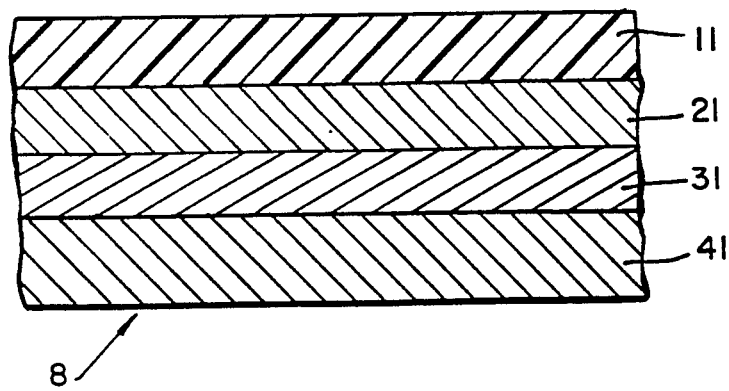
FIG. 2 is a cross-sectional view of a pharmacologically active agent delivery device in accordance with our invention consisting of four layers; a backing layer, a reservoir, a rate controlling membrane and an adhesive as used in Example II, infra.

Referring to the device of FIG. 2, a backing 11 has adhered to one surface thereof a pharmacologically active agent-containing reservoir layer 21. Adhered to the surface of the pharmacologically active-containing reservoir on a surface opposite to the backing is the rate controlling membrane of our invention 31. Adhered to the rate controlling membrane 31 is an adhesive layer 41 with the entire article being indicated by reference numeral 8.

Structures similar to the structure of FIG. 2 are utilized in the practice of the inventions embodied by U.S. Pat. Nos. 4,201,211 and 4,060,084, the disclosures of which are incorporated by reference herein.

Structures such as that set forth in FIG. 2 may be utilized in conjunction with transdermal control release articles using scopolamine and clonidine.

The pharmacologically active-containing reservoir may comprise from about 20 up to about 60% by weight of the vinyl resin, from about 20 up to about 70% by weight of plasticizer composition and from about 0.5 up to 35% by weight of pharmacologically active agent, and the remainder being other excipients, such as materials which will enhance skin penetration.

Thus, Examples of skin penetration enhancers useful in the practice of our invention are the substance 1-dodecylhexahydro-2H-azepin-2-one (also known as AZONE ®) having the structure:

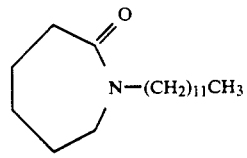

AZONE ® acts as both a plasticizer and an agent which enhances transdermal penetration of pharmacologically active agents. By the same token, N,N-diethyltoluamide having the structure:

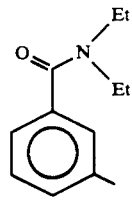

acts in the same manner as AZONE ® and may be used as a penetration enhancer in the practice of the instant invention.

Figure 3:
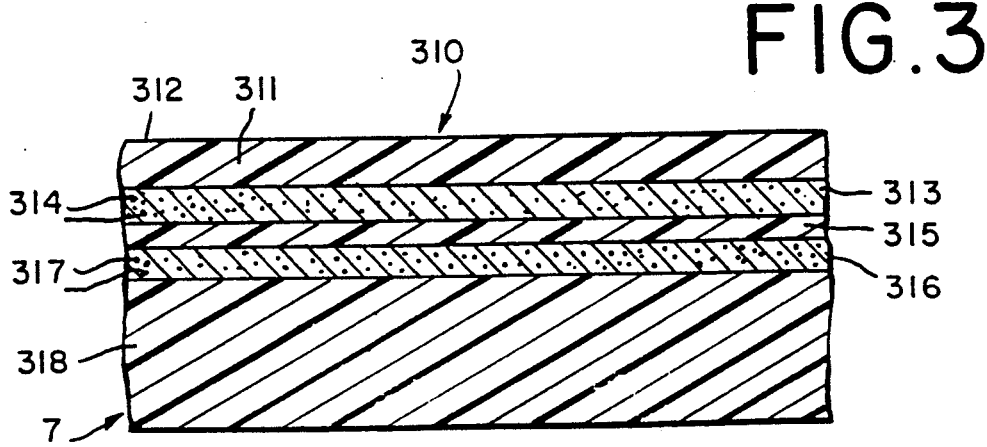
FIG. 3 is a cross-sectional view of a pharmacologically active agent delivery device in accordance with our invention showing the use of the control membrane of our invention in conjunction with the article of U.S. Pat. No. 4,060,084 issued on Nov. 29, 1977.

In the alternative, also useful in the practice of our invention is a structure of the type set forth in FIG. 3. Referring now to FIG. 3, the skin patches generally designated by reference numeral 310 has a construction which is a 5-layer laminate. The top layer 311 is a backing that is substantially impermeable to the pharmacologically active agent contained in the pharmacologically active agent-containing reservoir 313. The face 312 forms the top surface of the patch. Backing 311 serves as a protective covering keeping the volatile components of the patch from escaping and fulfills a support function. Preferably, backing layer 311 is itself a laminate of films of polymer and metal foil, such as aluminum foil. Polymers that may be used in the layer are high and low density polyethylene, polypropylene, polyvinyl chloride and polyethylene terephthalate.

Below and adjacent to layer 311 is a pharmacologically active agent-containing reservoir layer 313. Layer 313 contains from about 1 up to about 10 mg of pharmacologically active agents, e.g., clonidine, the undissolved portion of which is depicted as particles 314. The pharmacologically active agent contained in layer 313 is delivered to the blood during the constant administration portion of the dosage program. Particles 314 are dispersed homogeneously in a gelled mixture of an organic, apolar, nonvolatile inert liquid, such as mineral oil of about 10 to about 100 cp at 25° C. and a blend of polyisobutenes. The inert liquid will usually constitute 35% to 65% by weight of the mixture and the polyisobutene will correspondingly usually constitute 35% to 65% by weight of the mixture. The polyisobutene blend comprises a low molecular weight polyisobutene (35,000–50,000 viscosity average molecular weight) and a high molecular weight polyisobutene (1,000,000–1,500,000 viscosity average molecular weight). Preferred mixtures comprise 35% to 65% mineral oil, 10% to 40% lower molecular weight polyisobutene and 10% to 40% high molecular weight polyisobutene. These oil-polyisobutene mixtures are excellent adhesives to help hold the patch together.

The inert liquid (mineral oil) in layer 313 functions as a carrier for the pharmacologically active agent, e.g., clonidine. It is preferable that the inert liquid be one in which the pharmacologically active agent, e.g., clonidine, has limited solubility (for instance, its solubility in mineral oil is approximately 0.5 mg/ml) and the relative amounts of each in layer 313 be such that the inert liquid is saturated with the pharmacologically active agent, e.g., clonidine, for essentially the entire dispensing lifetime of the patch.

The next lamina in the patch is the microporous protective membrane of our invention 315 lamina, the control membrane lamina consisting essentially of a polymeric composition of matter which consists essentially of at least one $C_2$–$C_4$ lower olefin, $C_1$–$C_8$ alkyl acrylate and/or methyl acrylate copolymer having 2–90% by weight of alkyl acrylate and/or methacrylate monomeric units, taken alone or taken further together with, in intimate admixture, another polymeric composition consisting essentially of a $C_2$–$C_4$ polyalkylene corresponding to the $C_2$–$C_4$ lower alkylene of the copolymer. Membrane 315 is the element of the patch that controls the rate at which the pharmacologically active agent, e.g., clonidine, is released from layer 313. The flux of the pharmacologically active agent, e.g., clonidine, through membrane 315 and the area of membrane 315 must be such that the pharmacologically active agent, e.g., clonidine, is released from reservoir layer 313 to the skin at a substantially constant rate in the range of, for example, 0.1 up to 100 mcg/hr after the patch has been put in use. The flux follows Fick's law and is a function to the tortuosity, porosity and thickness of the membrane, the concentration gradient of the pharmacologically active agent, e.g., clonidine, across the membrane and the diffusion coefficient of the pharmacologically active agent, e.g., clonidine, in the inert liquid. The concentration gradient depends on the pharmacologically active agent, e.g., clonidine, concentrations in the inert liquid at the opposite sides of the membrane. The diffusion coefficient depends on the inert liquid viscosity and decreases with increasing viscosity. The three properties of the membrane are, of course, constant for any given membrane. Membranes that have porosities of from about 0.1 to 0.85, tortuosities from 1 to 10, and thicknesses of $10^{-3}$ to $10^{-2}$ cm may be used.

Below and adjacent membrane 315 is a contact adhesive lamina 316. Lamina 316 contains 10 to 300 mcg of pharmacologically active agent per $cm^2$ effective surface area. The undissolved portion of the pharmacologically active agent, e.g., clonidine, is depicted as particles 317. The pharmacologically active agent in lamina 316 is administered as the priming dose in this particular embodiment of our invention. The pharmacologically active agent is dispersed homogeneously in the same inert liquid, polyisobutene mixture that is used in layer 313. Lamina 316 is the means by which the patch is attached to the skin. In this regard, the inert liquid-polyisobutene mixture adheres less strongly the skin than it does to other laminas of the patch; therefore, the patch tends to remain intact when it is pulled off the skin.

Prior to use, the patch of FIG. 3 also includes a strippable protective coating 318 that covers lamina 316. Just prior to use, coating 318 is peeled away from lamina 316 and discarded. It may be made from pharmacologically active agent-inert liquid impermeable materials, such as the polymers from which backing 311 is made with the proviso that these materials are made strippable, such as by siliconizing.

The patch indicated by reference numeral 310 and by reference numeral 7 may be produced in the same manner as the production set forth at column 6, lines 10–68 and column 7, lines 1–6 of U.S. Pat. No. 4,201,211, the specification for which is incorporated by reference herein.

Referring to FIGS. 4, 5, 6, 7, 8 and 9, in the embodiments set forth herein and represented by these figures, polyvinyl chloride resins are employed.

When using polyvinyl chloride resins, it is preferred that the polyvinyl chloride resins employed in the practice of the present invention are those which are specifically used in preparing polyvinyl chloride "plastisols" namely PVC resins which are made by the well known emulsion polymerization process, which are hard spheres of particle size between 0.05 and 20 microns, such as between 1 and 20 microns, for example, between 1 and 5 microns, or between 0.05 and 1 micron, and which do not have the ability to absorb plasticizers to any great extent. Instead, the plasticizer wets the resin particles at room temperature and only then very slowly penetrates and solvates the resin. These PVC resins when mixed with plasticizers, such as a mixture of 30% primary plasticizer, 70% PVC resin, give a flowable liquid known as plastisol which can then be fused at, for example, approximately 250° F. for approximately 30 seconds to provide a solid polymer layer.

Thus, the PVC resin preferably employed in the present invention is in contrast to the general purpose PVC resins which are produced by suspension or bulk polymerization and which are used in calendering and extrusion processes, which are 50 to 200 microns, such as 100 to 150 microns in diameter, and are like sponges. Thus, the general purpose resins are capable of absorbing large amounts of plasticizers so that even a 50% DOP and 50% PVC resin would result in a non-flowing solid material. The molecular weight of the PVC resins employed in the present invention preferably is a weight average molecular weight between 80,000 and 250,000, such as a weight average molecular weight of 123,000. A suitable polyvinyl chloride resin is one sold by Occidental Chemical Co. under the designation FPC 6338 containing about 96% vinyl chloride monomer units of about 4% vinyl acetate monomer units. Thus, the polyvinyl chloride resin can be a copolymer containing preferably at least 90% by weight vinyl chloride monomer units, such as a copolymer based on vinyl chloride and vinyl acetate.

The polyvinyl chloride resin generally is present in the layer in an amount of 10 to 75 weight percent, preferably 20 to 70 weight percent, based on the total weight of the plasticized PVC composition.

The primary plasticizer which is employed in the present invention can be dioctylphthalate (DOP), benzylbutylphthalate, tri-2-ethylhexylmaleate, dioctyl adipate, epoxidized soybean oil, polymeric adipate plasticizers, which are polymers of adipic acid with a monomer, such as propylene glycol, and for example, can be obtained under the designation Drapex 334F from Witco Chemical Corp., or any other known primary plasticizer for PVC, which is biologically acceptable.

The other examples of polyester adipates, glutarates and sebacates are:
   polyester adipate P-644;
   polyester glutarate P-530;
   polyester glutarate P-540;
   polyester glutarate P-550;
   polyester glutarate P-7035;
   polyester glutarate P-7035M;
   polyester glutarate P-7046;
   polyester glutarate P-7092; and
   polyester sebacate P-1070
manufactured by the C. P. Hall Co., 7300 S. Central Avenue, Chicago, Ill. 60638. Other preferred plasticizers are those which are known as "adipate" plasticizers, for example, ADMEX ® 760 which is a high molecular weight (MW=8000) adipate plasticizer manufactured by the Sherex Division of Nuodex Inc. In general, polyester plasticizers which are polyesters of (i) 1,4-terephthalic acid and/or 1,2-phthalic acid and/or adipic acid with (ii) ethylene glycol, or 1,3-propylene glycol having molecular weights in the range of 4000–10,000 are preferred.

Another preferred plasticizer which also acts as a skin penetrating enhancer for pharmacologically active drugs which are intended for transdermal delivery from devices such as those set forth in FIGS. 1, 5 and 6 is the compound having the structure:

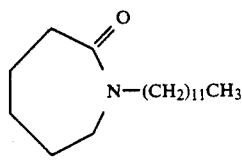

known as AZONE ® marketed by the Nelson Research and Development Co. The composition comprising PVC and the compound having the structure:

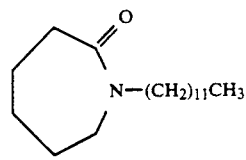

is a novel composition of matter.

Mixtures of known plasticizers can be used. The term "primary plasticizer" as used herein refers to a plasticizer which can be used alone to effect plasticization and is highly compatible with PVC at high concentrations, such as, for example, 150 parts per hundred. Primary plasticizers are contrasted with "secondary plasticizers" which, because of limited compatibility with PVC, cannot be used alone. See, Kirk-Othmer Encyclopedia of Chemical Technology, Volume 23, 3rd Edition, especially pages 913 and 914 for a discussion of primary and secondary plasticizers, which is incorporated by reference herein.

The primary plasticizer generally is present in an amount of 20 to 85 weight percent, preferably 20 to 70% based on the total weight of the plasticized PVC layer.

The plasticized PVC (preferably the PVC "plastisol") may optionally contain other additives or "excipients" useful in the practice of this invention, for example, material which enhance skin penetration of the pharmacologically active substances (e.g., 1,6-hexanediol and n-decyloleate) and thickeners, e.g., silica (preferably "fumed" silica, for example, AEROSIL ® in an amount of from 1–6% of the layer).

With reference to FIG. 4, a blended PVC plastisol 43 (the preferred form of the plasticized PVC) containing, for example, PVC, DOP and nitroglycerin is then coated at a rate of about 36 ounces/yd$^2$ on a backing 44 and then fused into solid plastisol layer 43. The backing 44 may be a single layer of drug-impermeable plastic or other material. Layer 44 may be MYLAR ® (polyester produced from ethylene glycol and phthalic anhydride) about 0.5 mils thick, and layer 43 may be PVC, about 4 mils thick. The backing 44 substantially blocks loss of drug from the plastisol layer 43 other than in the direction of the surface which in use will contact the rate controlling membrane.

The blended plastisol which is coated on the backing can be fused into a homogeneous solid by heating it for a short period, such as 15 to 30 seconds, at a temperature of, for example, 250° to 280° F. The use of a plastisol to form solid layer 43 enables layer 43 to be formed by using a low temperature for a short period of time, and provides conditions which do not affect the stability of the pharmacologically active agents.

A strip of solid plastisol layer 43 and backing 44 is then bonded to rate controlling membrane 42 composed of, for example, a copolyer of 7% ethylene repeating monomeric units and 93% methyl acrylate repeating monomeric units. The resulting strip of solid plastisol layer 43, backing 44 and rate controlling membrane 42 is then bonded to a pressure-sensitive adhesive layer 45 which, in turn, is provided with a non-adhesive backing 46, such as one made of plastic, moisture-proof fabric, aluminum foil, etc.

When not in use, the entire surface intended for skin contact is preferably covered with a release paper 47 or the like which is removed to expose surfaces of the adhesive layer 45 and drug containing plastisol layer 43 for application to the patient's skin.

FIG. 6 shows a plan view of a strip of material during the stage of manufacture at which a strip of the plastisol 53 (backing 44 and rate controlling membrane 42 not shown) has been applied to the adhesive tape (adhesive layer 55 shown) (backing 46 not shown). For the preferred device for the controlled administration of pharmacologically active agent, e.g., indomethacin, isosorbide dinitrate, nicotine, clonidine, glyceryl trinitrate, guanfacine or prostaglandin, a plastisol strip preferably about one inch (1") in width is applied on a two and one-half inch (2½") wide pressure-sensitive adhesive strip.

FIG. 7 shows a plan view of a strip of the material 630 in accordance with this invention; spaced lines 631 may be embossed or printed on the surface away from skin contact so that the patient may conveniently measure out and cut off the proper amount of tape device to provide the prescribed daily dosage. For a device for administering the pharmacologically active agent, e.g., nitroglycerin, for example, a segment 1" long cut from the longer tape (resulting in an approximately one square inch (1 sq. in.) of active surface against the patient's skin) will provide a dosage of about 17 mg/24 hours; this is believed to be an enhanced rate of delivery compared with commercially available transdermal drug delivery devices and also will provide the patient with a bandage device having a surface area much smaller than found in previously available devices.

Figure 8:
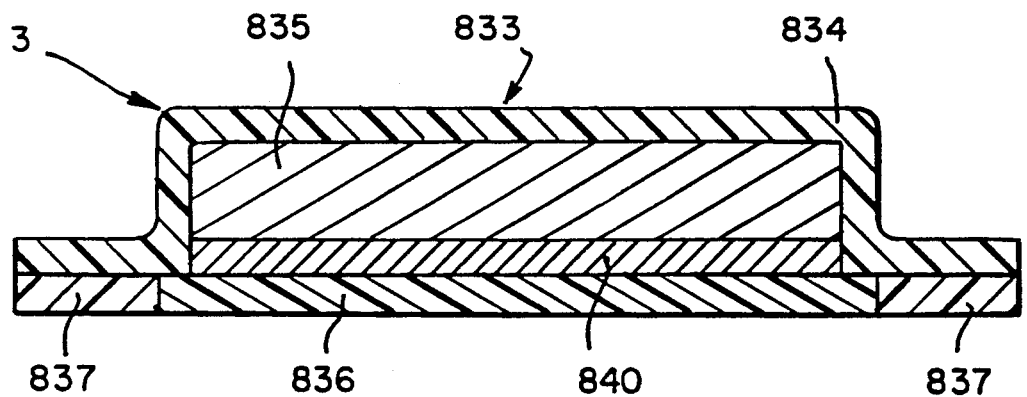
FIG. 8 is an enlarged sectional schematic view of a specific embodiment of our invention; a transdermal device for controlled release of a pharmacologically active agent from a plasticized polyvinyl chloride monolayer through the control membrane of our invention, transdermally.

Referring to FIG. 8, the components of embodiment 833 (and also shown using reference numeral 3) are backing layer 834, a reservoir layer 835 that contains supplies of percutaneous absorption enhancer and pharmacologically active substance, such as indomethacin, diffusion membrane layers 836 and 840 and a peripheral ring 837 of contact adhesive. The diffusion membrane layers are composed of a polymer such as a copolymer of ethylene and methyl acrylate with the methyl acrylate being in the range of 2–90% by weight of the polymer or blends of such copolymer with low density polyethylene, high density polyethylene or linear low density polyethylene. The contact adhesive component of embodiment 833 is in the form of a peripheral ring 837. Optionally, backing layer 834 may also be a semipermeable membrane. Neither the pharmacologically active agent, e.g., isosorbide dinitrate nor enhancer passes through ring 837 and it therefore need not be permeable to those compositions. Optionally, the contact adhesive may be attached directly to the membrane 836 in which case the adhesive is selected so that it is permeable to the active agent.

Figure 9:
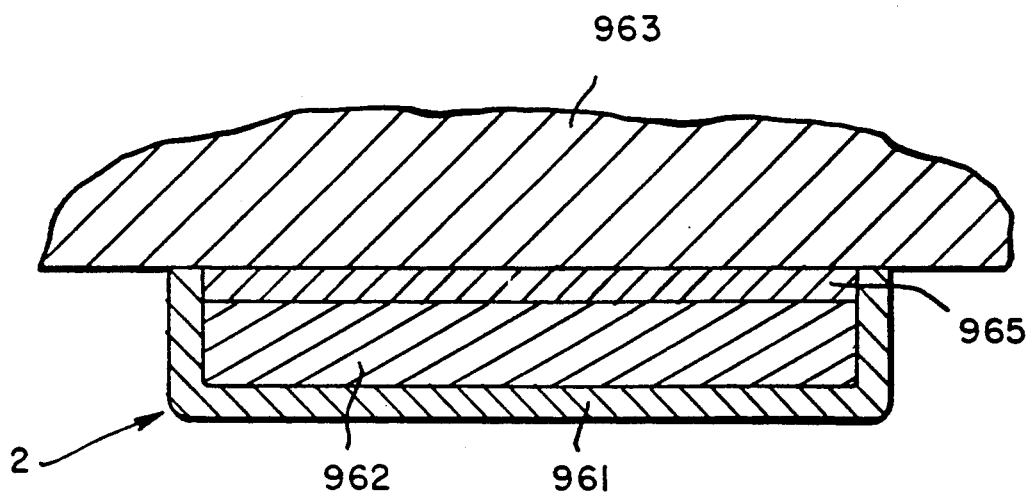
FIG. 9 is an enlarged sectional schematic view of another embodiment of our invention where there is a control membrane separating the plasticized polyvinyl chloride monolayer from the epidermis and whereby pharmacologically active agent is transported from the plasticized polyvinyl chloride transdermally through the control membrane into the patient.

Secondly, the basil surface from which the pharmacologically active substance and enhancer (e.g., AZONE ®) is transferred to the skin is defined by diffusion membrane layer 836. The backing layer is not flat but instead forms a pocket or cavity in which the reservoir layer is held. The outer edge of the backing layer is sealed to the peripheral ring of the contact adhesive as more specifically set forth in U.S. Pat. No. 4,379,454 issued on Apr. 12, 1983, the disclosure of which is incorporated herein by reference. Similarly, an article within the contemplation of our invention is illustrated in FIG. 9 wherein the backing 961 totally surrounds the PVC-plastisol-plasticizer matrix 962 and rate controlling membrane 965 and is firmly in place as with an adhesive on the skin 963.

As shown in FIG. 7, the device of the invention may conveniently be provided in the form of a tape roll 950 from which daily dosage requirements may be clipped by the patient.

The device is capable of application to humans or other animals capable of usefully absorbing drugs through the skin.

Other embodiments of our invention are those useful in, for example, U.S. Pat. Nos. 4,573,996 and 4,573,995 issued on Mar. 4, 1986, the specifications for which are incorporated by reference herein.

Figure 10:
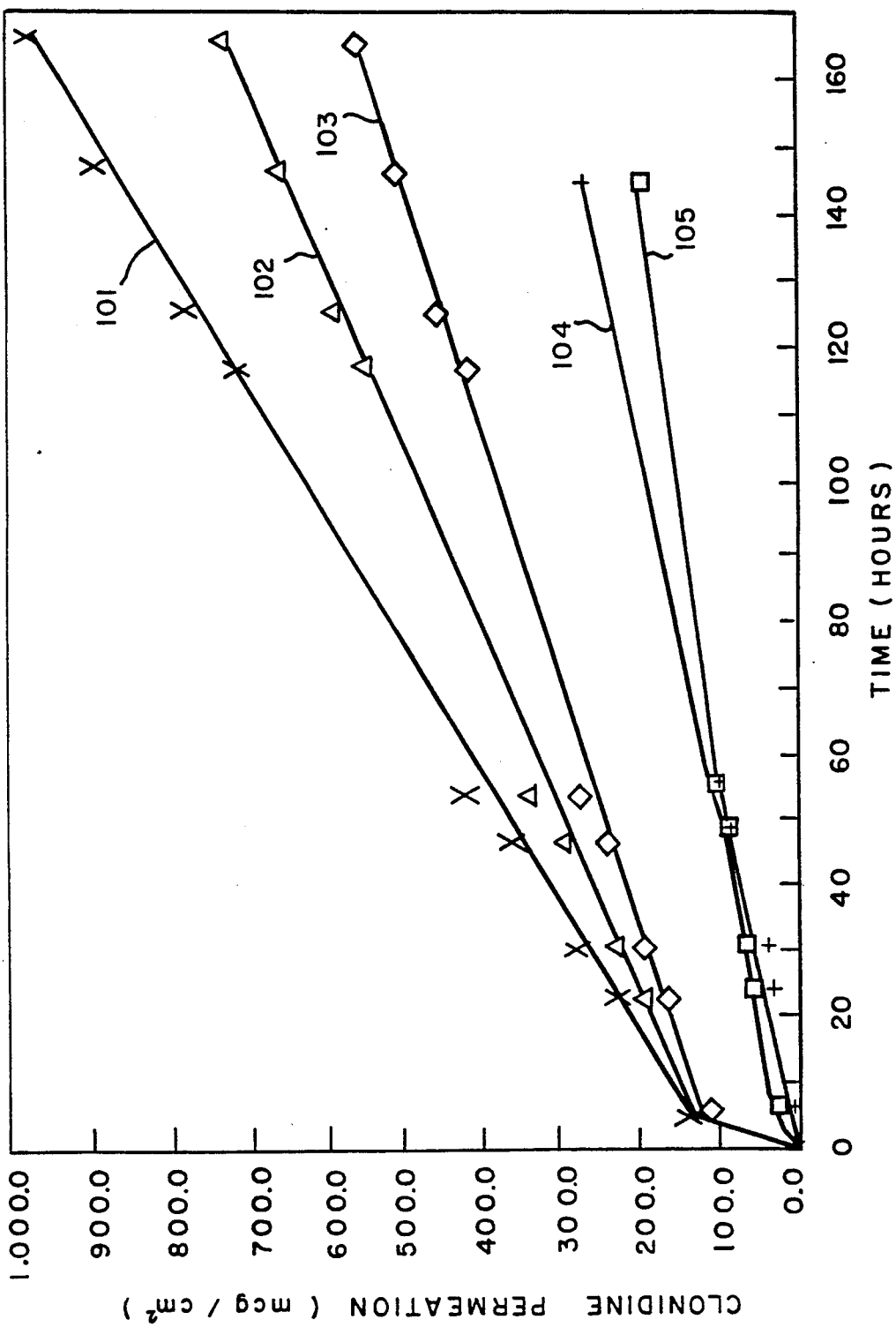
FIG. 10 is a series of graphs showing clonidine permeation in mcg/cm versus time (hours) through the epidermis of human cadaver skin from articles of our invention having different proportions of methyl acrylate to polyethylene in the copolymer (e.g., 5%, 7%, 13%, 15% and 18%) as more specifically set forth in Example III, infra.

FIG. 10 is a series of graphs showing clonidine permeation in mcg/cm versus time (hours) through the epidermis of human cadaver skin from articles of our invention having different proportions of methyl acrylate to polyethylene and the copolymer. Thus, the graph indicated by reference numeral 101 is for 18% methyl acrylate in the copolymer. The graph indicated by reference numeral 102 is for 15% methyl acrylate in the copolymer. The graph indicated by reference numeral 103 is for 13% methyl acrylate in the copolymer. The graph indicated by reference numeral 104 is for 7% methyl acrylate in the copolymer and the graph indicated by reference numeral 105 is for 5% methyl acrylate in the copolymer.

The graphs of FIG. 10 are more specifically described in Example III, infra.

Figure 11:
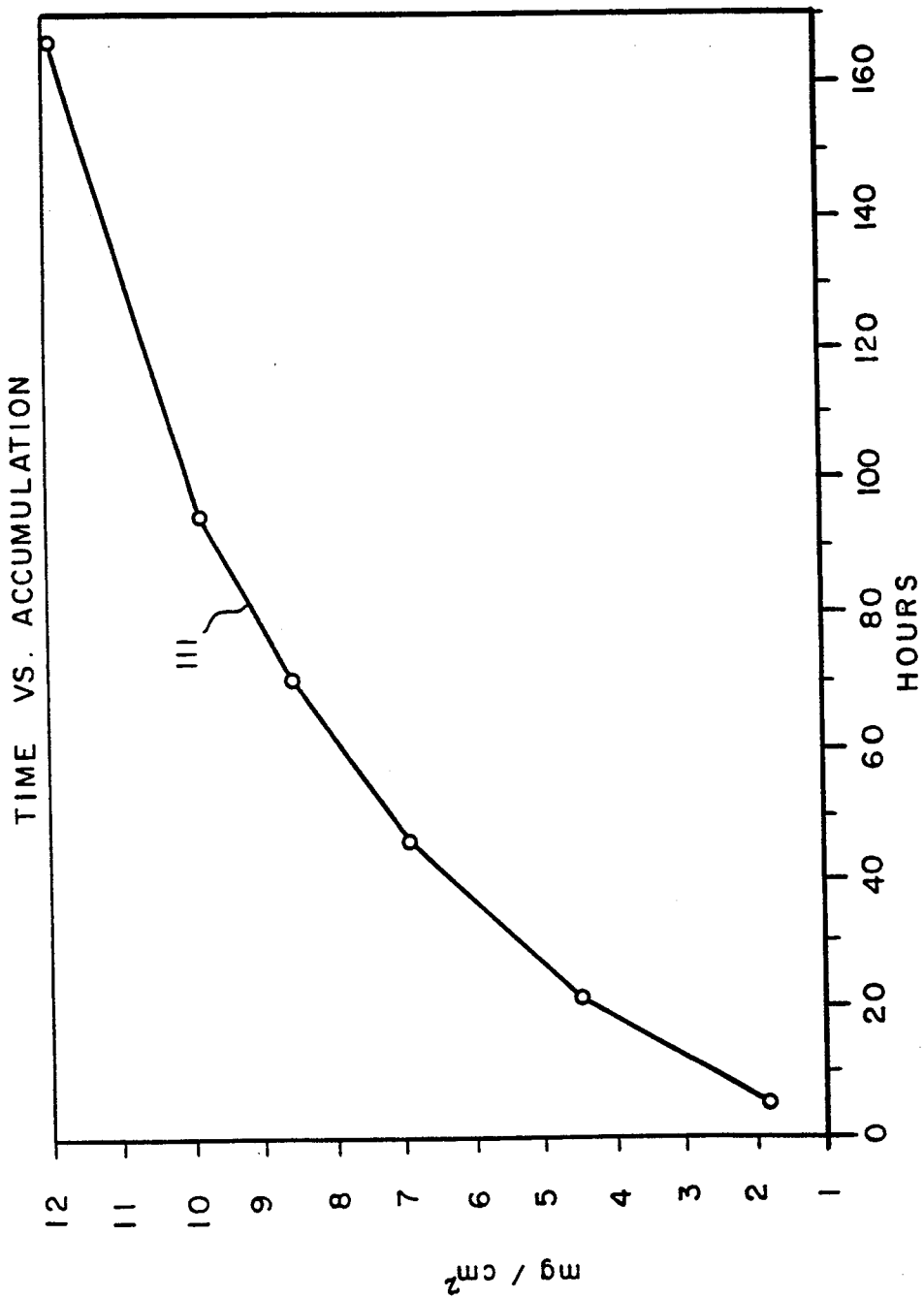
FIG. 11 is a graph of timolol release versus time (time versus accumulation) from an ADMEX ®760 reservoir without the use of a control membrane (as set forth in Example IV).

FIG. 11 is a graph of timolol release versus time (time versus accumulation) from an ADMEX ® 760 reservoir without the use of a control membrane as set forth in Example IV. The graph indicated by reference numeral 111 is the graph of $mg/cm^2$ of timolol release versus hours. The basis of this graph is more specifically set forth in Example IV.

Figure 12:
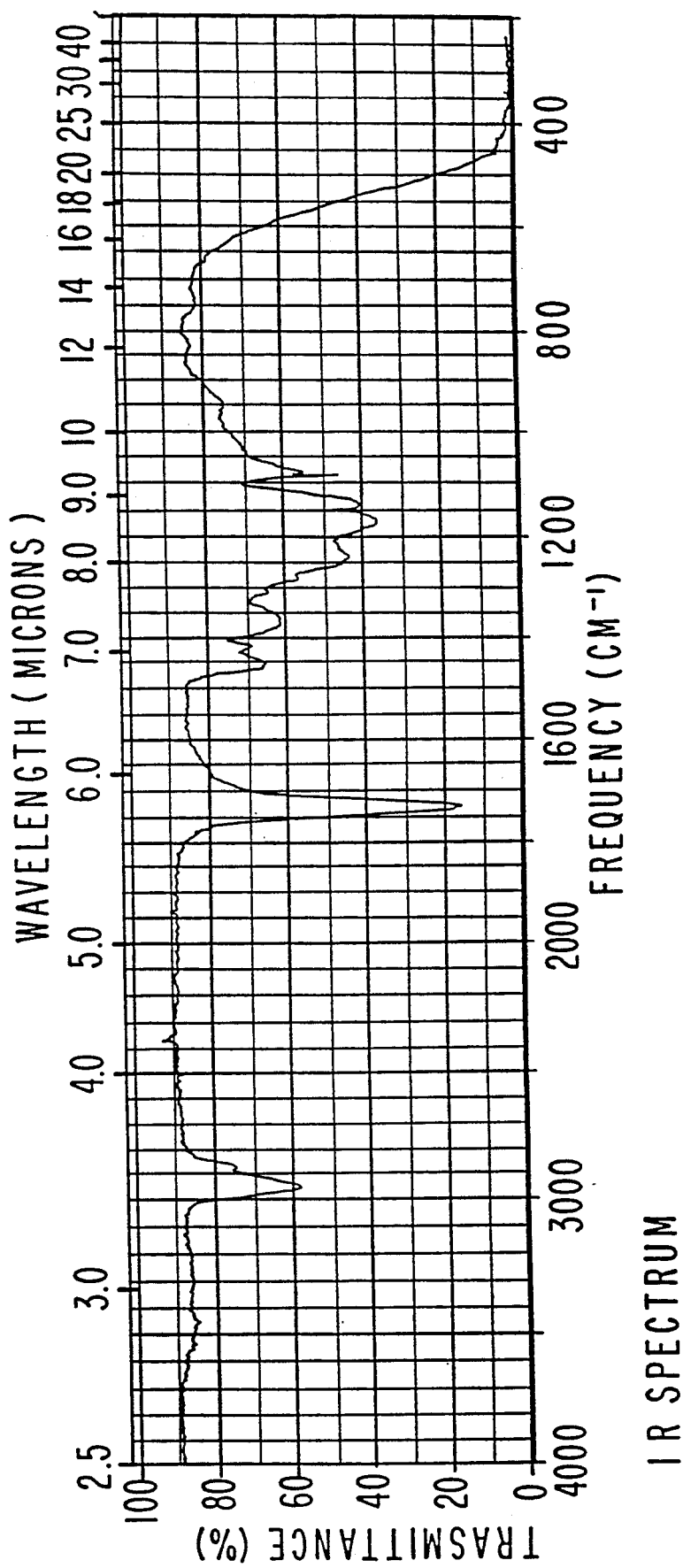
FIG. 12 is the infrared spectrum of ADMEX ®760 as used in the examples herein.

FIG. 12 is the infrared spectrum of ADMEX ® 760 as used in the examples herein.

Figure 13:
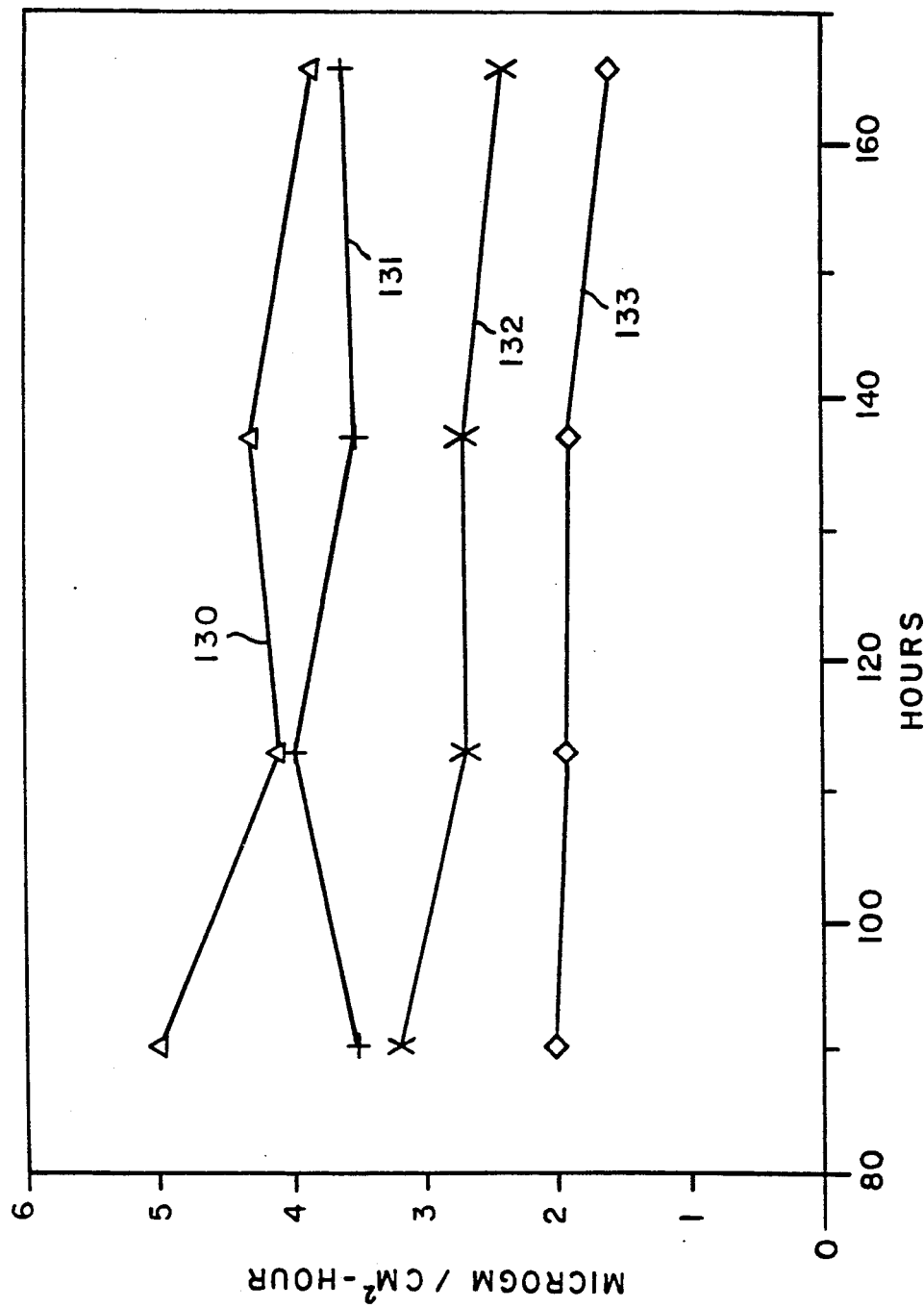
FIG. 13 is a series of graphs (time versus flux) of timolol release rate through control membranes consisting of copolymers of ethylene and methyl acrylate; 5% and 7% with 1.25 mils thickness and 2.5 mils thickness as more specifically set forth in Example IV.

FIG. 13 is a series of graphs (time versus flux) of timolol release rate through control membranes consisting of copolymers of ethylene and methyl acrylate; 5% and 7% with 1.25 mils thickness and 2.5 mils thickness as more specifically set forth in Example IV. The graph indicated by reference numeral 130 is the graph for a membrane having 7% methyl acrylate repeating monomeric units and a membrane of thickness 1.25 mils. The graph indicated by reference numeral 131 is the graph for use of a membrane containing 5% methyl acrylate repeating monomeric units with a thickness of 1.25 mils. The graph indicated by reference numeral 132 is the graph for the use of a membrane containing 7% methyl acrylate repeating monomeric units and having a thickness of 2.5 mils. The graph indicated by reference numeral 133 is the graph for a membrane containing 5% methyl acrylate repeating monomeric units and having a thickness of 2.5 mils.

Figure 14:
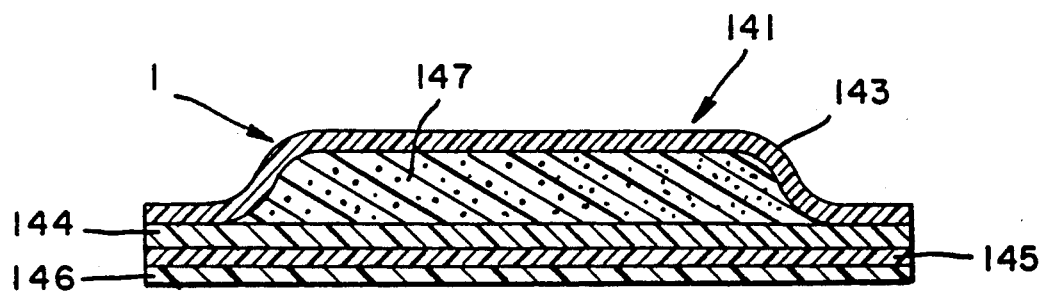
FIG. 14 is a cross-sectional view of a pharmacologically active agent delivery device using the olefin-acrylate copolymer membrane of our invention in conjunction with the high flux transdermal therapeutic system of U.S. Pat. No. 4,615,699 issued on Oct. 7, 1986.

FIG. 14 is a cross-sectional view of a pharmacologically active agent delivery device using the olefin-acrylate copolymer membrane of our invention in conjunction with the high flux transdermal therapeutic system of U.S. Pat. No. 4,615,699 issued on Oct. 7, 1986 incorporated herein by reference. Thus, with respect to the article indicated by reference numeral 1, the system 1 is preferably fabricated in the form of a laminated pouch formed from an impermeable backing 143 bonded at its periphery 2, and spaced apart at its central portion from a pharmacologically active agent release rate controlling membrane 144 of our invention (ethylene-methyl acrylate copolymer, for example) which is coated with a contact adhesive 145 provided with a protective removable liner 146 intended to be stripped from the device prior to use. Although the preferred embodiment illustrated herein shows the use of an in-line adhesive 145, other means for holding the system in pharmacologically active agent and permeation enhancer transmitting relationship to the skin include circumferentially located adhesives, adhesive overlays, belts, buckles, elastic bands or the like. The pouch is filled with a composition 147 which comprises the pharmacologically active agent and permeation enhancer reservoir preferably in the form of a viscous gel or paste. Certain critical interrelationships between the compositions of membrane 144 and the drug-enhancer reservoir 147 of the transdermal pharmacologically active agent delivery system must exist in accordance with this aspect of our invention. The variables which are critical are specifically set forth in U.S. Pat. No. 4,615,699 at columns 3, 4 and 5 and such disclosure is incorporated herein by reference.

Figure 15:
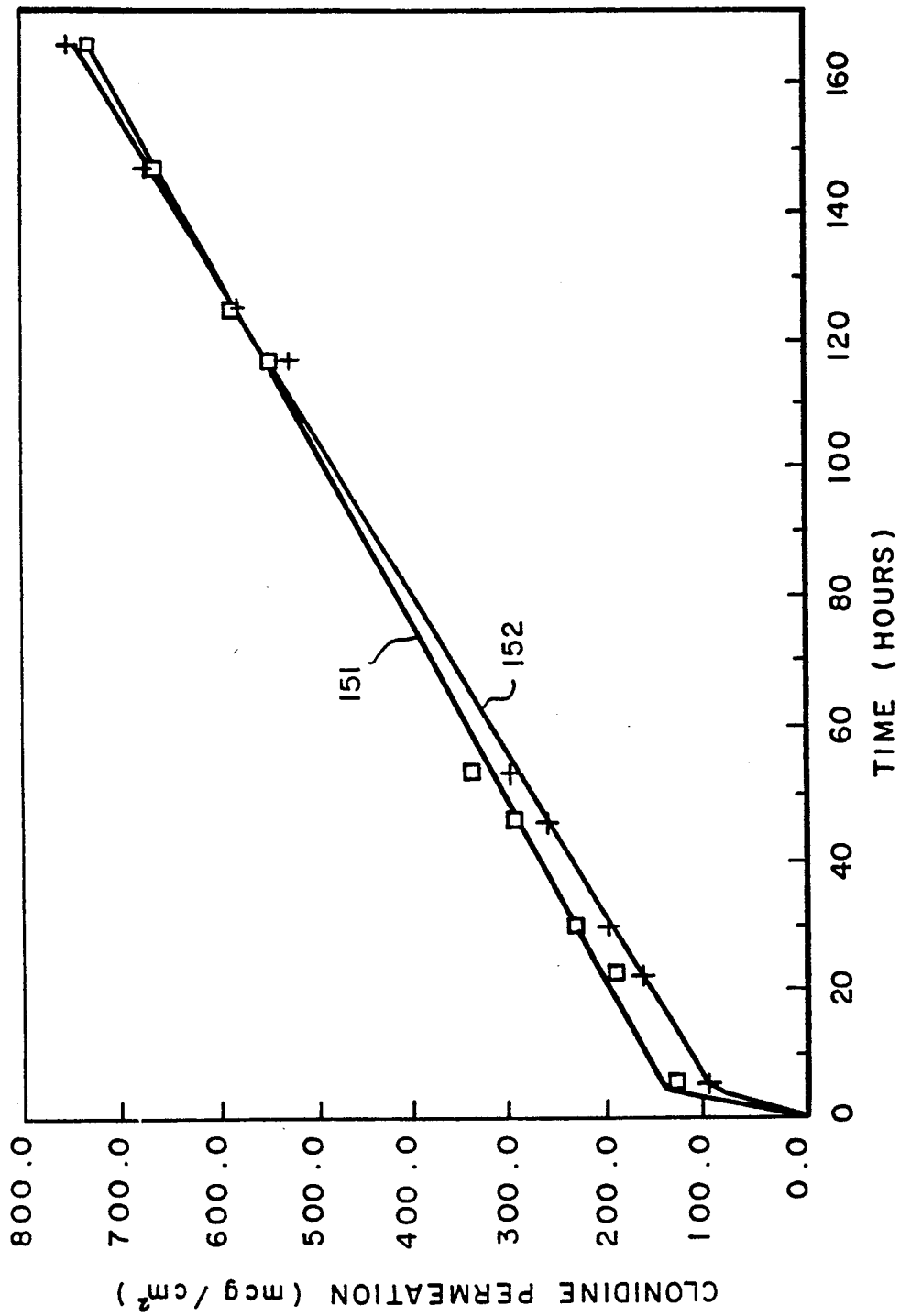
FIG. 15 is a graph of clonidine permeation (mcg/cm$^2$) versus time (hours) for the in vitro permeation of clonidine through the epidermis of human cadaver skin from a patch containing 15% ethylene-methyl acrylate copolymer and from a patch containing a microporous polypropylene membrane (sold under the designation CELGARD 2400 ®) disclosed in U.S. Pat. No. 4,201,211 issued on May 6, 1980 using an article of the type described in the example of U.S. Pat. No. 4,201,211 issued on May 6, 1980.

FIG. 15 is a graph of clonidine permeation (mcg/cm$^2$) versus time (hours) for the in vitro permeation of clonidine through the epidermis of human cadaver skin from a patch containing 15% ethylene-methyl acrylate copolymer and from a patch containing a microporous polypropylene membrane (sold under the designation CELGARD 2400 ®) disclosed in U.S. Pat. No. 4,201,211 issued on May 6, 1980 using an article of the type described in the example of U.S. Pat. No. 4,201,211 issued on May 6, 1980, the disclosure of which is incorporated herein by reference.

The graph indicated by reference numeral 151 is the graph for clonidine permeation versus time using the membrane of our invention containing 15% methyl acrylate repeating monomeric units. The graph indicated by reference numeral 152 is the graph using the microporous polypropylene membrane (sold under the designation CELGARD 2400 ®) (CELGARD 2400 ® has a thickness of 25 microns).

Figure 16:
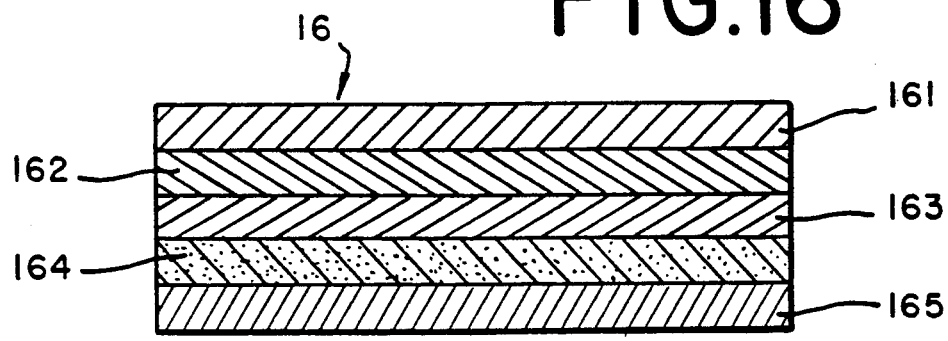
FIG. 16 is a cross-sectional view of a preferred pharmacologically active agent delivery device in accordance with our invention having five layers; a barrier membrane, a reservoir, a control membrane, a pressure-sensitive adhesive and a release liner.

FIG. 16 is a cross-sectional view of another preferred pharmacologically active agent delivery device in accordance with our invention having five layers; a barrier layer 161; a pharmacologically active agent-containing reservoir 162; a control membrane consisting essentially of a polymeric composition of matter which consists essentially of one $C_2$–$C_4$ lower olefin, $C_1$–$C_8$ alkyl acrylate and/or methacrylate having 2-90% by weight of alkyl acrylate and/or methacrylate monomeric units taken alone or taken further together with in intimate admixture another polymeric composition consisting essentially of a $C_2$–$C_4$ polyalkylene corresponding to the $C_2$–$C_4$ lower of the copolymer; a pressure-sensitive adhesive coated on the control membrane 164; a release liner for use in connection with the pressure-sensitive adhesive 165. The article of FIG. 16 is indicated using reference numeral 16.

Figure 17:
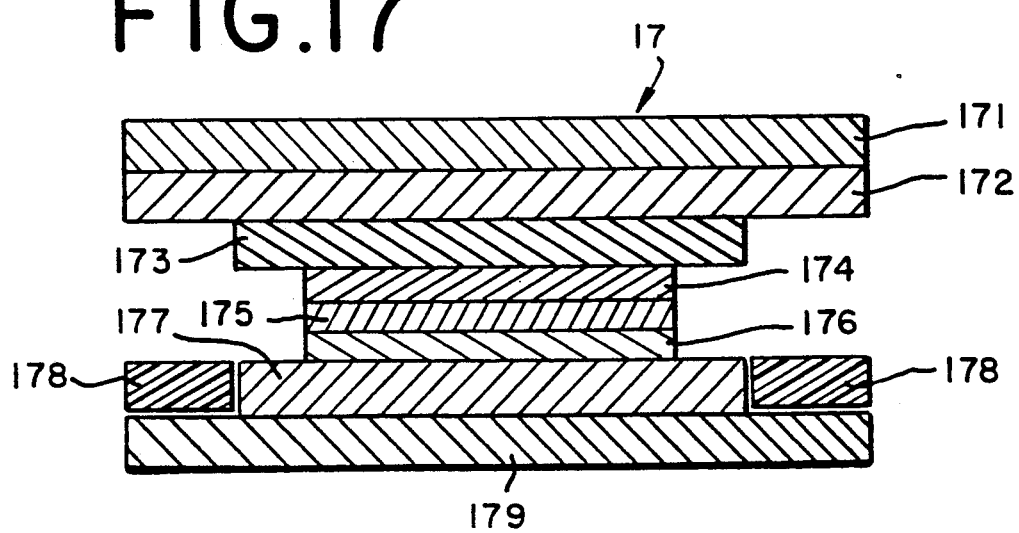
FIG. 17 is a cross-sectional view of another preferred pharmacologically active agent delivery device in accordance with our invention having eight layers; a pressure-sensitive adhesive backing, a pressure-adhesive, a heat sealable membrane, a barrier membrane, a reservoir, a control membrane, a heat sealable membrane (with release liner) and an aluminum foil barrier.

FIG. 17 is a cross-sectional view of another preferred pharmacologically active agent delivery device in accordance with our invention having eight layers; a pressure-sensitive adhesive backing 171; a pressure sensitive adhesive 172; a heat sealable membrane 173 bonded to the pressure-sensitive adhesive 172; a barrier membrane 174 bonded to the heat sealable membrane 173; a pharmacologically active agent containing reservoir 175 bonded to the barrier membrane 174; a control membrane 176 bonded to the pharmacologically active agent containing reservoir 175 which control membrane consists essentially of a polymeric composition of matter which consists essentially of at least one $C_2$–$C_4$ lower olefin/$C_1$–$C_8$ alkyl acrylate and/or methacrylate copolymer having 2-90% by weight of alkyl acrylate and/or methacrylate monomeric units taken alone or taken further together with in intimate admixture a third polymeric composition consisting essentially of a $C_2$–$C_4$ polyalkylene corresponding to the $C_2$–$C_4$ lower alkylene of the copolymer; a heat sealable membrane 177 bonded to the control membrane; a release liner 178; and an aluminum foil barrier 179 bonded to the release liner.

Figure 18:
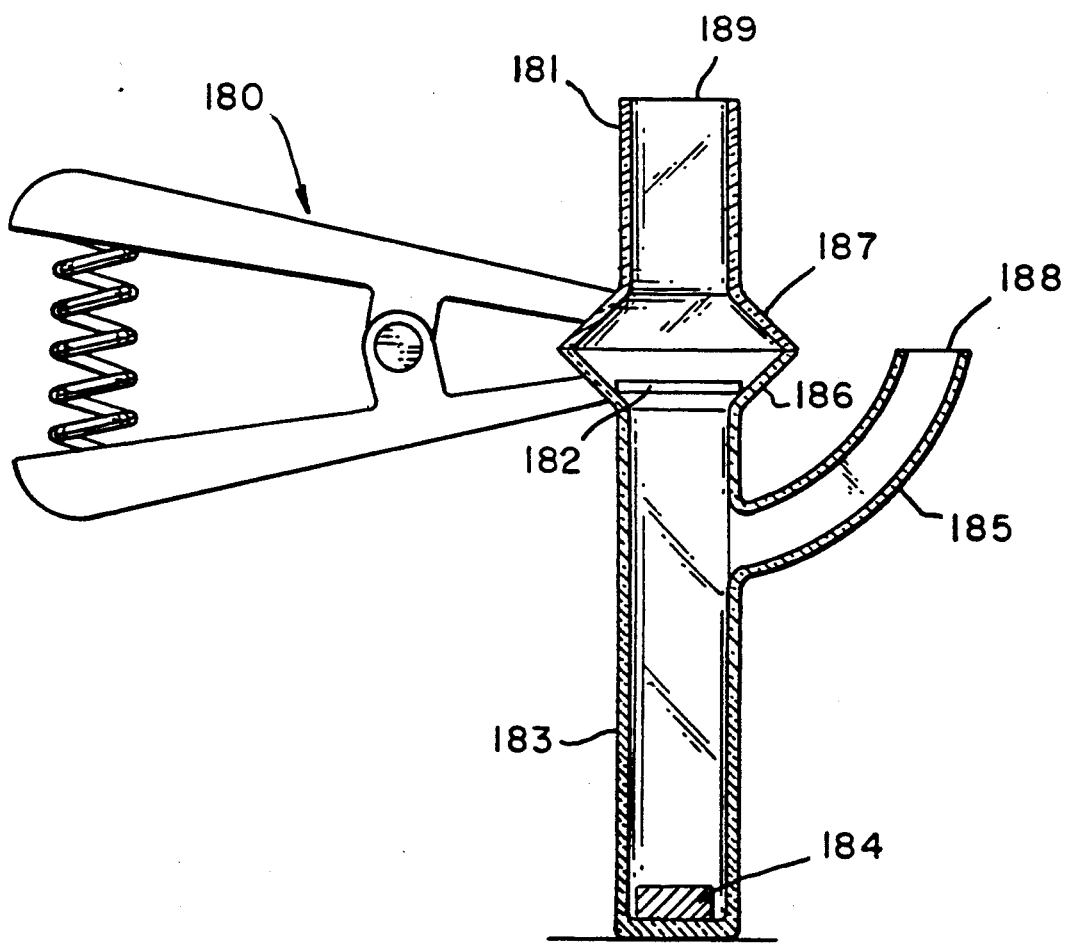
FIG. 18 is a cut-away cross-sectional view of a franz-type diffusion cell with pinched clamp indicating the means for testing the devices in order to supply the data for the examples herein.

FIG. 18 is a schematic diagram of a Franz type diffusion cell and pinch clamp used in conjunction with the measurements set forth in the examples provided herein, infra. The pinch clamp indicated by reference numeral 180 holds the upper part of the Franz diffusion cell 181 at surface 187 to the lower part of the Franz diffusion cell 183 at location 186 while measuring the permeability of, for example, a membrane 182 which is held in place by the upper and lower parts of the diffusion cell 181 and 183, respectively. The pharmacologically active agent contained in the article whose permeability is to be measured, 182, is contacted with liquid contained in 183 and stirred by means of stirring bar 184. Sample is withdrawn through sampling tube 185 at sampling port 188 thereby measuring concentrations over a period of time of pharmacologically active agent dissolved in the fluid contained in container 183 as a result of contact of the liquid with the article 182. For the purposes of this invention, the only utility of upper section 181 is to hold in place the article which is the subject of the measurement, 182. Thus, no liquid is added for the purposes of the examples in this invention, through port 189.

Figure 19:
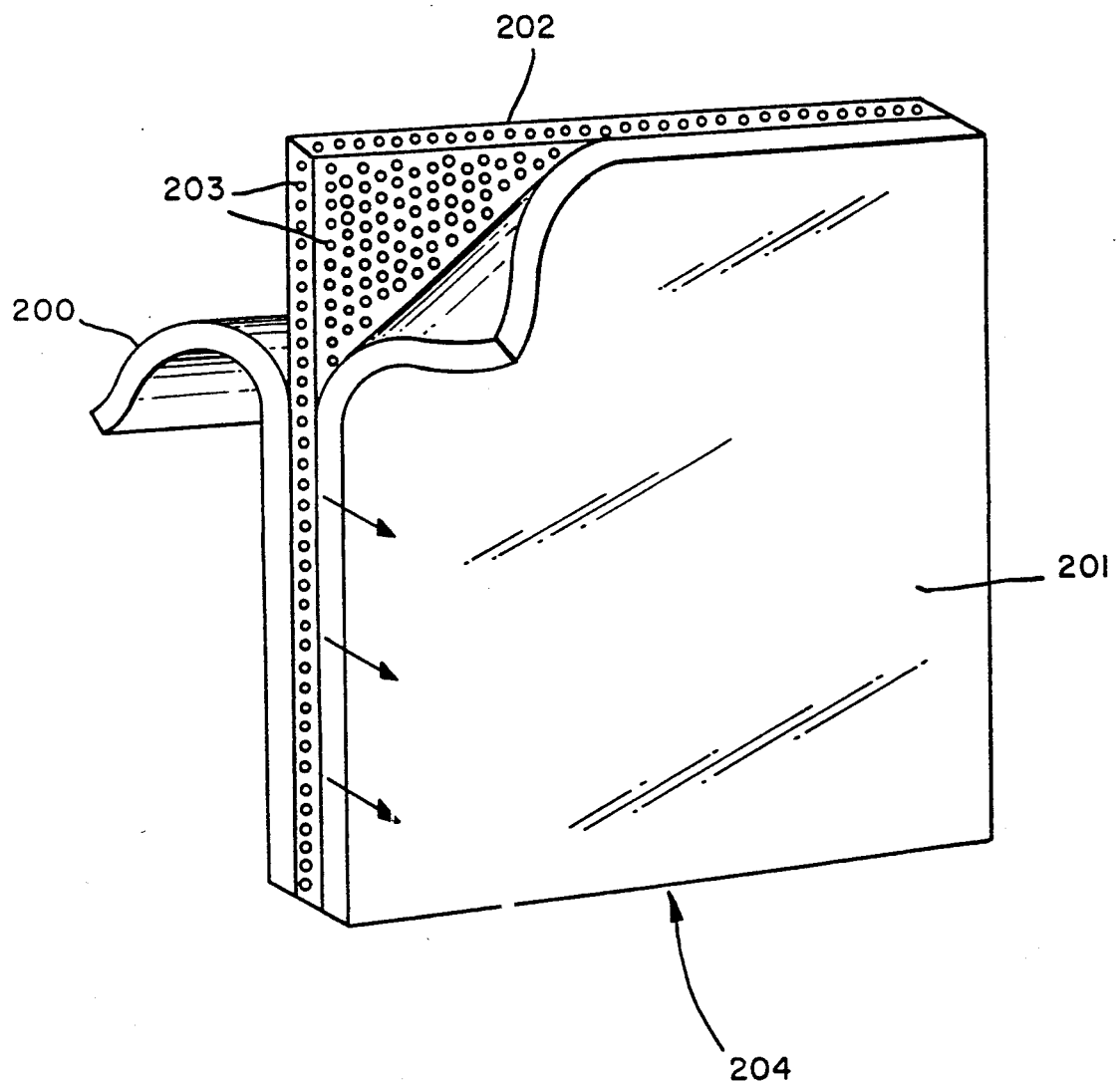
FIG. 19 is a perspective view of a partially opened article of a pharmacologically active agent delivery device in accordance with our invention indicating that controlled amounts of active agent move from the reservoir layer to the surface and indicating subsequent diffusion through the control membrane.

FIG. 19 is a perspective view of a partially opened article of a pharmacologically active agent delivery device in accordance with our invention indicating that controlled amounts of active agent move from the reservoir layer 202 to the surface and indicating subsequent diffusion through the control membrane 201. Controlled amounts of active agent shown by the dots 203 move from the reservoir layer 202 through the control membrane 201. The article is indicated by reference numeral 204. The backing layer is indicated by reference numeral 200. The backing layer is actually a barrier to the flow of drug in a direction opposite to that indicated by the arrows in FIG. 19.

EXAMPLE I

Transdermal Treatment of Hypertension Using Clonidine Patches

The objective of this study is to determine how the drug release rate of clonidine from a transdermal patch of the type set forth in U.S. Pat. No. 4,292,303, the disclosure of which is incorporated herein by reference, is affected by the addition of a copolymeric rate controlling membrane (methylacrylate ethylene copolymer film indicated by "EMA") and an increase in the drug concentration. The experimental procedure used is the same as that set forth in U.S. Pat. No. 4,292,303.

Materials and Apparatus:

In the development of the transdermal patches for clonidine, the following chemicals were used: clonidine free base, glycerol, deionized water, polyvinylalcohol (PVA), and polyvinylpyrrolidone (PVP). The films utilized included: 1.5 mil thick silicone treated release MYLAR ® and 1.25 mil 7, 11, and 18% EMA. The experimental apparatus consists of Franz-type diffusion cells having a diffusion surface area of 0.732 cm² and a receptor volume of 5.5 mil.

Experimental Procedure:

A total of 8 patches, 4 containing 2% drug and 4 containing 10% drug were made. Both sets of 4 patches were comprised as follows: 1 patch without a membrane, a second with 7% EMA, a third with 11% EMA and a fourth with 18% EMA, each patch consisting of two or three layers. The three-layer patches are illustrated in FIG. 1.

The reservoir layers were formulated as follows:

| Component | Reservoir 1 (%) | Reservoir 2 (%) |
|---|---|---|
| clonidine | 2.0 | 10.0 |
| glycerol | 30.0 | 26.0 |
| deionized water | 45.0 | 41.0 |
| PVA | 15.0 | 15.0 |
| PVP | 8.0 | 8.0 |
| | 100.0 | 100.0 |

Each reservoir layer was prepared by first mixing thoroughly the glycerol and water components. The mixture was then heated up to 90° C. During the heating period at 70° C., the PVA and PVP were slowly added. Consequently, this mixture was stirred at 90° C. until a homogeneous solution was obtained. Afterwards, it was cast upon 1.5 mil thick silicone treated release MYLAR ® and allowed to air cool at room temperature for four hours resulting in a reservoir layer approximately 40 mil thick. This matrix was then cut into four pieces and the patches prepared as follows: without a microporous membrane, with 7% EMA, 11 % EMA, and 18% EMA.

Patch Characteristics:

| Drug % | EMA Membrane (% MA) | Layer Thickness (mil) |
|---|---|---|
| 2 | — | 45 |
| 2 | 7 | 46.3 |
| 2 | 11 | 40.3 |
| 2 | 18 | 39.3 |
| 10 | — | 38.0 |
| 10 | 7 | 38.0 |
| 10 | 11 | 40.0 |
| 10 | 18 | 41.0 |

Dissolution Experiment:

At the completion of the 8 patches, a dissolution study was conducted using diffusion cells. The cells were maintai.ed at temperature of 34° C. and contained the receptor phase: an aqueous mixture of citric acid and sodium phosphate. Drug diffusion samples were analyzed through high pressure liquid chromatography (HPLC) method developed for clonidine. The HPLC method used includes ¹⁸Cu Bonda Pak columns and Tetra Butyl Ammonium Phosphate:Acetonitrile in the ratio of 40:60 as the mobile phase.

Results:

A comparison of drug release rates for Key and EMA (Hercon) clonidine patches is shown below. The values represent the average constant drug release rate over a period of two days.

| Patch | Key (mg/hr) (from Patent Example) | EMA (Hercon 10 cm² patch) (mg/hr) |
|---|---|---|
| 2% drug without a membrane | 0.4 | 0.5 |
| 2% drug and 7% EMA | — | 0.003 |
| 2% drug and 11% EMA | — | 0.012 |
| 2% drug and 18% EMA | — | 0.07 |
| 10% drug without a membrane | — | 1.43 |
| 10% drug and 7% EMA | — | 0.003 |
| 10% drug and 11% EMA | — | 0.014 |
| 10% drug and 10% EMA | — | 0.05 |

Conclusions:

The copolymeric EMA membranes were found to lower the drug diffusion rates in the transdermal patch even at higher clonidine concentrations.

EXAMPLE II

Transdermal Treatment of Hypertension and Motion Sickness Using Clonidine or Scopolamine The objective of this investigation is to determine if the required drug release rates, for clonidine and scopolamine, are maintained when a microporous rate-controlling membrane used in accordance with U.S. Pat. Nos. 4,201,211 and 4,060,084 (incorporated by reference herein) is replaced by an ethylene-methyl acrylate copolymer film (herein indicated as "EMA"). The experimental procedure used is the same as that set forth in U.S. Pat. No. 4,201,211 incorporated by reference herein.

Materials and Apparatus:

In the development of the transdermal patches, the following chemicals were used: clonidine free base, scopolamine free base, light mineral oil, n-heptane, chloroform, deionized water, Vistanex MML-100, Vistanex LM-MS, citric acid (monohydrate), and sodium phosphate (dibasic). The films utilized include: 1.5 mil thick silicone treated release MYLAR ®, 3 mil Scotchpak (#1006-Fleshtone), 1.25 mil 7, 11, and 18% EMA. The experimental apparatus consists of Franz-type diffusion cells having a diffusion surface area of 0.732 cm² and a receptor volume of 5.5 mil.

Experimental Procedure:

A total of three patches was made for each drug. For clonidine, one patch used 7% EMA, another 11% and the third 18%. A similar distribution was utilized for scopolamine. Each patch consisted of four layers as set forth in FIG. 2.

The reservoir and adhesive layers were formulated as follows:

For Clonidine:

| Component | Reservoir (%) | Adhesive (%) |
|---|---|---|
| Clonidine | 2.9 | 0.9 |
| Mineral Oil | 10.4 | 11.4 |
| n-Heptane | 75.0 | 75.0 |
| Vistanex MML-100 (a polyisobutylene resin manufactured by Exxon Chemical Co. | 5.2 | 5.7 |

-continued

| Component | Reservoir (%) | Adhesive (%) |
|---|---|---|
| of Linden, N.J. having a viscosity average molecular weight (Flory) of 1,200,000 and a viscosity average molecular weight (Staudinger) of 81,000–99,000) | | |
| Vistanex LM-MS | 6.5 | 7.0 |
| (a polyisobutylene resin manufactured by Exxon Chemical Co. of Linden, N.J. having a viscosity average molecular weight (Flory) of 40,000 and a viscosity average molecular weight (Staudinger) of 8,700–10,000) | | |
| | 100.0 | 100.0 |

For Scopolamine:

| Component | Reservoir (%) | Adhesive (%) |
|---|---|---|
| scopolamine | 1.57 | 0.46 |
| mineral oil | 5.85 | 6.36 |
| chloroform | 86.02 | 86.02 |
| Vistanex MML-100 | 2.92 | 3.18 |
| (a polyisobutylene resin manufactured by Exxon Chemical Co. of Linden, N.J. having a viscosity average molecular weight (Flory) of 1,200,000 and a viscosity average molecular weight (Staudinger) of 81,000–99,000) | | |
| Vistanex LM-MS | 3.65 | 3.98 |
| (a polyisobutylene resin manufactured by Exxon Chemical Co. of Linden, N.J. having a viscosity average molecular weight (Flory) of 40,000 and a viscosity average molecular weight (Staudinger) of 8,700–10,000) | | |
| | 100.0 | 100.0 |

Each formulation was allowed to mix well on a shaker until all its components went into solution. After homogeneous mixtures were obtained, reservoir layers were cast upon 3 mil Scotchpak (#1006) while adhesive layers were cast upon 1.5 mil silicone treated release MYLAR ®. Once cast, these four layers were allowed to air dry overnight and then oven dry for 15 minutes at 60° C. After drying, each reservoir layer was cut into three pieces and laminated to one side of 7, 11 and 18% EMA, respectively. Similarly, adhesive layers were cut into three pieces and laminated to the other sides of the 7, 11 and 18% EMA-reservoir system thus forming the transdermal patch.

Patch Characteristics:

| Drug | EMA Membrane (% MA) | Patch Layer | Layer Thickness (mil) |
|---|---|---|---|
| clonidine | 7 | Reservoir | 2.1 |
| | | Adhesive | 1.75 |
| clonidine | 11 | Reservoir | 2.1 |
| | | Adhesive | 1.60 |
| clonidine | 18 | Reservoir | 2.2 |
| | | Adhesive | 1.60 |
| scopolamine | 7 | Reservoir | 2.3 |
| | | Adhesive | 1.5 |
| scopolamine | 11 | Reservoir | 2.3 |
| | | Adhesive | 1.6 |
| scopolamine | 18 | Reservoir | 2.3 |
| | | Adhesive | 1.6 |

Dissolution Experiment:

At the completion of the six patches, a dissolution study was conducted using diffusion cells. The cells were maintained at a temperature of 35° C. and contained the receptor phase: an aqueous mixture of citric acid and sodium phosphate. Drug diffusion samples were analayzed through a high pressure liquid chromatography (HPLC) method developed for each drug. The HPLC procedure used for clonidine includes [18]Cu Bonda Pak columns and Tetra Butyl Ammonium Phosphate:Acetonitrile in the ratio of 40:60 as the mobile phase. A similar method is utilized for scopolamine consisting of Spherisorb columns and $NH_4H_2PO_4$: Acetonitrile in the ratio of 60:40 as the mobile phase.

Results:

A comparison of drug release rates for CELGARD ®(Alza) and EMA (Hercon) patches for clonidine and scopolamine is shown below. The values represent the average constant drug rate over a period of two days.

| Patch | CELGARD ® (Alza) ($mcg/cm^2/hr$) (From Patent Example) | EMA (Hercon) ($mcg/cm^2/hr$) |
|---|---|---|
| Clonidine with Celgard 2400 | 2.7 | — |
| Clonidine with 7% EMA | — | 0.48 |
| Clonidine with 11% EMA | — | 1.74 |
| Clonidine with 18% EMA | — | 2.81 |
| Scopolamine with CELGARD ® 2400 | 3–3.5 | — |
| Scopolamine with 7% EMA | — | 3.1 |
| Scopolamine with 11% EMA | — | 4.2 |
| Scopolamine with 18% EMA | — | 9.5 |

Conclusions:

The copolymeric EMA membranes have been found to provide an alternate effective laminate system for the clonidine transdermal patch.

EXAMPLE III

Determination of Clonidine Penetration Versus Time Using Methyl Acrylate-Ethylene Copolymer Control Membrane In carrying out this example, we have studied in vitro transdermal delivery of clonidine from patches having the structure set forth in FIG. 17. These studies were conducted on the epidermis of human cadaver skin utilizing Franz-type diffusion cells as set forth in FIG. 18 with an aqueous buffer solution (pH 5.0) of citric acid/disodium hydrogen phosphate as the receptor phase at 31° C.

The patch construction was of the face adhesive type in which the layer of polymeric matrix containing the drug was laminated to a flexible polyester barrier film on one side and a rate controlling membrane with an acrylic pressure sensitive adhesive on the other side.

The rate controlling membranes investigated were olefinic copolymers containing the methyl acrylate repeating monomeric unit in various proportions.

The effect of the polar modification of the membrane copolymer upon the rate of transport of clonidine from the patch and through the skin is summarized in Table I and graphically illustrated in FIG. 10.

A proportionate increase in the clonidine flux through the skin with an increasing amount of methyl acrylate in the olefinic copolymer membrane was observed. The rate of drug delivery was constant throughout the seven-day period for all the different patches modified with methyl acrylate repeating monomeric units. It was also found that one of the patches (membrane copolymer with 15% modifier) exhibited a drug transport profile similar to that of microporous polypropylene as indicated in FIG. 15.

The flux values obtained from the patch containing the ethylene-methyl acrylate copolymer control membrane was 3.77±0.09 and the flux value obtained from the use of the patch containing the microporous polypropylene is 4.09±0.13 mcg/cm²/hr.

TABLE I

EFFECTIVE OF POLAR MODIFICATION OF THE MEMBRANE COPOLYMER UPON THE RATE OF CLONIDINE DELIVERED ACROSS HUMAN CADAVER SKIN FROM PATCHES HAVING METHYL ACRYLATE-ETHYLENE COPOLYMER AS CONTROL MEMBRANES

| Weight Percent Methyl Acrylate in Membrane Copolymer | Flux of Clonidine (mcg/cm²/hr) |
|---|---|
| 5 | 1.24 ± 0.12 |
| 7 | 1.90 ± 0.56 |
| 13 | 2.73 ± 0.09 |
| 15 | 3.77 ± 0.09 |
| 18 | 5.28 ± 0.26 |

EXAMPLE IV

Ethylene-Methyl Acrylate Copolymer Based Films as Rate Controlling Membranes for Transdermal Drug Delivery Devices for Delivery of Timolol A transdermal delivery device for a drug whose permeation rate through skin is much greater than that required to maintain a therapeutic level of its concentration in blood plasma generally requires a semi-permeable membrane to control the drug delivery rate. An appropriate membrane must possess selective permeability, chemical and physical stability, inertness to the chemical and biological environment, biocompatibility, adequate mechanical integrity and ease of processability.

In this example, we have found that copolymers of ethylene and methyl acrylate exhibit similar material and permeation characteristics to those of ethylene-vinyl acetate copolymers; which make them suitable for use as membranes for transdermal drug delivery. The ethylene-methyl acrylate membranes can have a methyl acrylate content ranging from 2 to 90% by weight. The membranes may also be composed of blends of an ethylene methyl acrylate copolymer with either low density polyethylene, high density polyethylene or linear low density polyethylene.

Release behavior of timolol from a polymeric reseroir is altered by the use of ethylene methyl acrylate membranes.

FIG. 11 shows that in the absence of a membrane the release of timolol from a polymeric reservoir into an aqueous sink is very high and followed typical first order kinetics.

FIG. 13 shows the effect of ethylene-methyl acrylate membranes of various thickness and methyl acrylate content upon the release of timolol from the same reservoir. Relatively controlled and constant release of the drug was obtained for a period of seven days.

EXAMPLE V

For the purposes of Examples V (A), V (B) and V (C), articles having the structure set forth in FIG. 4 were used. The following results were obtained:

EXAMPLE V (A)

CLENBUTEROL

I. Reservoir Formulation:
   Drug . . . 5%
   PVC Resin . . . 35%
   ADMEX ®760 . . . 60%
II. Membrane:
   1.25 mil thick EMA (11% MA)
III. Flux Thru Human Skin:
   (ug/cm²/day)
   without membrane: 34.5
   with membrane: 15.1

EXAMPLE V (B)

SCOPOLAMINE

I. Reservoir Formulation:
   Drug . . . 10%
   PVC Resin . . . 35%
   ADMEX ®760 . . . 55%
II. Membrane:
   1.25 mil thick EMA (20% MA)
III. Flux Thru Human Skin:
   (ug/cm²/hour)
   Without membrane: 1.95
   With membrane: 0.32

EXAMPLE V (C)

CLONIDINE

I. Reservoir Formulation:
   Drug . . . 20%
   PVC Resin . . . 20%
   ADMEX ®760 . . . 60%
II. Membrane:
   1.25 mil thick EMA
III. Flux Thru Human Skin:
   (ug/cm²/hr.)
   Without membrane: 18.5
   With membrane:
      7% MA . . . 0.82
      11% MA . . . 3.5
      20% MA . . . 5.4

What is claimed is:

1. A device for the controlled release and delivery to mammalian tissue of a pharmacologically active agent comprising:
   (i) at least one polymeric reservoir lamina having a first reservoir lamina surface and, opposite thereto, a second reservoir lamina surface, said reservoir lamina consisting essentially of a first polymeric material and a pharmacologically active agent intimately admixed therewith, (a) said pharmacologically active agent being physically and chemically compatible with said first polymeric material and (b) said first polymeric material being capable of permitting release of said pharmacologically active agent from either said first reservoir lamina surface or said second reservoir lamina surface; and
   (ii) coated on at least a portion of said first reservoir lamina surface and/or said second reservoir lamina surface sufficient to provide a desired degree of control, a control membrane lamina having a first control membrane lamina surface and, opposite thereto, a second control membrane lamina surface, said control membrane lamina, prior to utilization of said device consisting essentially of a second polymeric material which consists essentially of at least one $C_2$–$C_4$ lower olefin-$C_1$–$C_8$ alkyl acrylate and/or methacrylate copolymer having 2–90% by weight of alkyl acrylate and/or methacrylate monomeric units, taken alone, or taken further together with, in intimate admixture, a third polymeric material consisting essentially of a $C_2$–$C_4$ polyalkylene corresponding to the $C_2$–$C_4$ lower alkylene of said copolymer, said third polymeric material being compatible with said second polymeric material, said control membrane lamina being juxtaposed with said polymeric reservoir lamina at said first control membrane lamina surface.

2. The device of claim 1 wherein said first polymeric material is plasticized polyvinyl chloride comprising by weight from about 20 up to about 70% of a polyvinyl chloride resin; from about 20 up to about 70% by weight of plasticizer and from about 0.5 up to about 35% of pharmacologically active substance.

3. The device of claim 1 wherein a backing member lamina, substantially impermeable to said pharmacologically active agent, is adhered to substantially the entire second reservoir lamina surface.

4. The device of claim 2 wherein the plasticizer is a polymeric plasticizer.

5. The device of claim 2 wherein the plasticizer is a monomeric plasticizer.

6. The device of claim 1 wherein the third polymeric material is selected from the group consisting of high density polyethylene, low density polyethylene and linear low density polyethylene.

7. The device of claim 4 wherein the polymeric plasticizer is epoxidized soybean oil.

8. The device of claim 1 wherein said second control membrane lamina surface comprises means to maintain skin contact between the skin of an animal to be treated and said second control membrane lamina surface whereby transdermal absorption of said pharmacologically active agent takes place.

9. The device of claim 2 wherein a backing member lamina, substantially impermeable to said pharmacologically active agent, is adhered to substantially the entire second reservoir lamina surface.

10. The device of claim 8 wherein said means to maintain skin contact is an adhesive layer for affixing to the skin of the animal to be treated.

11. The device of claim 1 wherein said second polymeric material contains the repeating monomeric units:

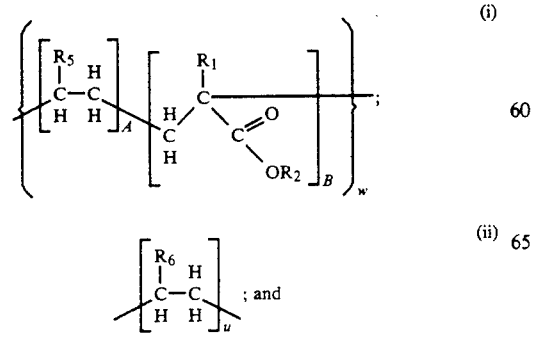

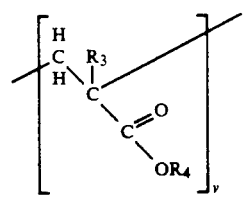

wherein $R_5$ and $R_6$ are the same or different hydrogen or methyl;

wherein $R_1$ and $R_3$ are the same or different hydrogen or methyl;

wherein $R_2$ and $R_4$ are the same or different methyl or ethyl;

wherein w, A, B, u and v are integers; and wherein the mole ratio of A+u:B+v varies about 10:90 to about 98:2.

12. The device of claim 1 wherein said second polymeric material is an ethylene-methyl acrylate copolymer having 2–90% by weight of methyl acrylate monomeric units.

13. The device of claim 1 wherein the pharmacologically active agent is selected from the group consisting of:
(i) clonidine or its salts;
(ii) scopolomine or its salts;
(iii) timolol;
(iv) clenbuterol;
(v) nicotine; and
(vi) fentanyl.

14. The device of claim 8 wherein said first polymeric material is plasticized polyvinyl chloride comprising by weight from about 20 up to about 70% of a polyvinyl chloride resin; from about 20 up to about 70% by weight of plasticizer and from about 0.5 up to about 35% of pharmacologically active substance.

15. The device of claim 14 wherein a backing member lamina, substantially impermeable to said pharmacologically active agent, is adhered to substantially the entire second reservoir lamina surface.

16. The device of claim 14 wherein the plasticizer is a polymeric plasticizer.

17. The device of claim 14 wherein the plasticizer is a monomeric plasticizer.

18. The device of claim 16 wherein the polymeric plasticizer is epoxidized soybean oil.

19. The device of claim 14 wherein a backing member lamina, substantially impermeable to said pharmacologically active agent, is adhered to substantially the entire second reservoir lamina surface.

20. The device of claim 14 wherein said second polymeric material contains the repeating monomeric units:

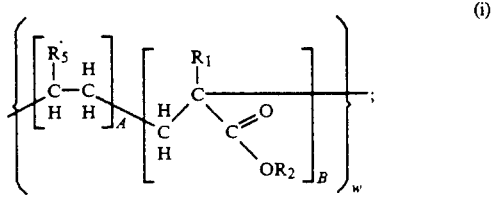

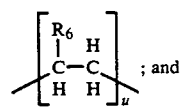

(ii)

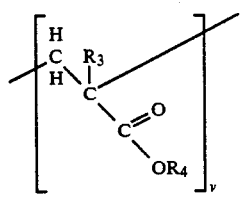

(iii)

wherein $R_5$ and $R_6$ are the same or different hydrogen or methyl;

wherein $R_1$ and $R_3$ are the same or different hydrogen or methyl;

wherein $R_2$ and $R_4$ are the same or different methyl or ethyl;

wherein w, A, B, u and v are integers; and wherein the mole ratio of A+u:B+v varies from about 10:90 to about 98:2.

21. The device of claim 14 wherein said second polymeric material is an ethylene-methyl acrylate copolymer having 2-90% by weight of methyl acrylate monomeric units.

22. The device of claim 14 wherein the pharmacologically active agent is selected from the group consisting of:
 (i) clonidine or its salts;
 (ii) scopolomine or its salts;
 (iii) timolol;
 (iv) clenbuterol;
 (v) nicotine; and
 (vi) fentanyl.

23. The device of claim 14 wherein the third polymeric material is selected from the group consisting of high density polyethylene, low density polyethylene and linear low density polyethylene.

24. A device for the subdermal controlled release and delivery to human tissue of a pharmacologically active agent comprising:
 (i) at least one polymeric reservoir lamina having a first reservoir lamina surface and, opposite thereto, a second reservoir lamina surface, said reservoir lamina consisting essentially of a first polymeric material and a pharmacologically active agent intimately admixed therewith, (a) said pharmacologically active agent being physically and chemically compatible with said first polymeric material and (b) said first polymeric material being capable of permitting release of said pharmacologically active agent from said first reservoir lamina surface and said second reservoir lamina surface, and
 (ii) coated on said first reservoir lamina surface and said second reservoir lamina surface, a control membrane lamina having a first control membrane lamina surface and, opposite thereto, a second control membrane lamina surface, said control membrane lamina, prior to utilization of said device consisting essentially of a second polymeric material which consists essentially of at least one $C_2$-$C_4$ lower alkylene-$C_1$-$C_8$ alkyl acrylate and/or methacrylate copolymer having 2-90% by weight of alkyl acrylate and/or methacrylate monomeric units, taken alone, or taken further together with, in intimate admixture, a third polymeric material consisting essentially of a $C_2$-$C_4$ polyalkylene corresponding to the $C_2$-$C_4$ lower alkylene of said copolymer, said third polymeric material being compatible with said second polymeric material, said control membrane lamina being juxtaposed with and surrounding said polymeric reservoir lamina at said first control membrane lamina surface.

25. A device for the controlled release and delivery to mammalian tissue of a pharmacologically active agent comprising:
 (i) an impermeable backing member;
 (ii) a control membrane lamina consisting essentially of a first polymeric material which consists essentially of at least one $C_2$-$C_4$ lower olefin-$C_1$-$C_8$ alkyl acrylate and/or methacrylate copolymer having 2-90% by weight of alkyl acrylate and/or methacrylate monomeric units, taken alone, or taken further together with, in intimate admixture, a second polymeric material consisting essentially of a $C_2$-$C_4$ polyalkylene corresponding to the $C_2$-$C_4$ lower alkylene of said copolymer, said second polymeric material being compatible with said first polymeric material;
 (iii) a pharmacologically active agent reservoir maintained therebetween comprising said pharmacologically active agent intimately admixed with a carrier therefor, said pharmacologically active agent being physically and chemically compatible with said first polymeric material and said second polymeric material; said pharmacologically active agent reservoir being capable of permitting release of said pharmacologically active agent from said reservoir through said control membrane lamina; and
 (iv) means for maintaining said device in pharmacologically active agent transmitting relationship to said mammalian tissue.

26. A device of claim 25 wherein a backing member lamina, substantially impermeable to said pharmacologically active agent and said carrier is releasably adhered to substantially the entire surface of said control membrane lamina.

27. The device of claim 25 wherein said control membrane lamina has a first control membrane lamina surface and opposite thereto a second control membrane lamina surface; and the first control membrane lamina surface is in contact with said pharmacologically active agent reservoir and said second control membrane lamina surface comprises means to maintain skin contact between the skin of an animal to be treated and said second control membrane lamina surface whereby transdermal absorption of said pharmacologically active agent takes place.

28. The device of claim 27 wherein said means to maintain skin contact is an adhesive layer for affixing to the skin of the animal to be treated.

29. The device of claim 25 wherein said second polymeric composition of matter contains the repeating monomeric units:

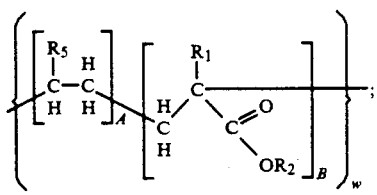
(i)

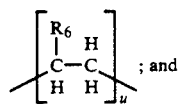
(ii)

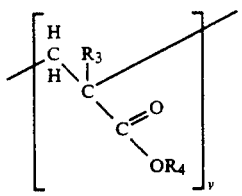
-continued
(iii)

wherein $R_5$ and $R_6$ are the same or different hydrogen or methyl;

wherein $R_1$ and $R_3$ are the same or different hydrogen or methyl;

wherein $R_2$ and $R_4$ are the same or different methyl or ethyl;

wherein w, A, B, u and v are integers; and wherein the mole ratio of A+u:B+v varies about 10:90 to about 98:2.

30. The device of claim 16 wherein the polymeric plasticizer is a polyadipate plasticizer.

31. The device of claim 1 wherein the first polymeric material is selected from the group consisting of plasticized polyvinyl chloride, a blend of polyisobutenes, and a mixture of polyvinyl alcohol and polyvinyl pyrrolidone.

* * * * *